(12) United States Patent
Papadopoulos et al.

(10) Patent No.: US 9,871,948 B2
(45) Date of Patent: Jan. 16, 2018

(54) METHODS AND APPARATUS FOR IMAGING WITH MULTIMODE OPTICAL FIBERS

(71) Applicant: ECOLE POLYTECHNIQUE FEDERALE DE LAUSANNE (EPFL), Lausanne (CH)

(72) Inventors: Ioannis Papadopoulos, Lausanne (CH); Salma Farahi, Lausanne (CH); Christophe Moser, Lausanne (CH); Demetri Psaltis, Préverenges (CH)

(73) Assignee: Ecole Polytechnique Fédérale de Lausanne (EPFL), Lausanne (CH)

( * ) Notice: Subject to any disclaimer, the term of this patent is extended or adjusted under 35 U.S.C. 154(b) by 325 days.

(21) Appl. No.: 14/389,275

(22) PCT Filed: Mar. 28, 2013

(86) PCT No.: PCT/IB2013/052493
§ 371 (c)(1),
(2) Date: Sep. 29, 2014

(87) PCT Pub. No.: WO2013/144898
PCT Pub. Date: Oct. 3, 2013

(65) Prior Publication Data
US 2015/0015879 A1    Jan. 15, 2015

(30) Foreign Application Priority Data

Mar. 29, 2012  (WO) .................. PCT/IB2012/051509

(51) Int. Cl.
*H04N 1/40*        (2006.01)
*G02B 6/028*       (2006.01)
(Continued)

(52) U.S. Cl.
CPC ............. *H04N 1/40* (2013.01); *G01J 3/0218* (2013.01); *G01J 3/44* (2013.01); *G02B 6/0288* (2013.01);
(Continued)

(58) Field of Classification Search
CPC .......... G01J 3/0218; G01J 3/44; G02B 23/26; G02B 26/06; G02B 27/58; G02B 6/0288;
(Continued)

(56) References Cited

U.S. PATENT DOCUMENTS 5,956,447 A     9/1999  Zel et al.
6,078,392 A *   6/2000  Thomas .............. G03H 1/0443
                                                    356/457
(Continued)

FOREIGN PATENT DOCUMENTS

WO         2010/004297 A1     1/2010

OTHER PUBLICATIONS

Neff et al. "Two-Dimensional Spatial Light Modulators: A Tutorial" Proceedings of the IEEE, vol. 78, No. 5, May 1990.*
(Continued)

*Primary Examiner* — Dominic J Bologna
(74) *Attorney, Agent, or Firm* — Nixon & Vanderhye P.C.

(57) ABSTRACT

A multimode waveguide illuminator and imager relies on a wave front shaping system that acts to compensate for modal scrambling and light dispersion by the multimode waveguide. A first step consists of calibrating the multimode wave ¬ guide and a second step consists in projecting a specific pattern on the wave¬ guide proximal end in order to produce the desire light pattern at its distal end. The illumination pattern can be scanned or changed dynamically only by chang¬ing the phase pattern projected at the proximal end of the waveguide. The third and last step consists in collecting the optical information, generated by the sample,
(Continued)

through the same waveguide in order to form an image. Known free space microscopy technique can be adapted to endoscopy with multimode waveguide, such as, but not limited to, fluorescence imaging or Raman spectroscopy or imaging, 3D linear scattering imaging or two-photon imaging. Super-resolution, i.e., resolution below the diffraction limit, is achieved for example but not limited to, using the STimulated Emission Depletion microscopy (STED) technique or the Structured Illumination Microscopy (SIM) technique or a stochastic illumination based method (PALM, STORM) in combination with the multimode waveguide imaging method.

39 Claims, 33 Drawing Sheets

(51) Int. Cl.
  *G02F 1/313* (2006.01)
  *G02F 1/01* (2006.01)
  *G01J 3/44* (2006.01)
  *G01J 3/02* (2006.01)
  *G02B 23/26* (2006.01)
  *G02B 26/06* (2006.01)
  *G03H 1/00* (2006.01)
  *G02B 27/58* (2006.01)
  *H04B 10/2581* (2013.01)
  *G03H 1/22* (2006.01)
  *G03H 1/04* (2006.01)

(52) U.S. Cl.
  CPC ............ *G02B 23/26* (2013.01); *G02B 26/06* (2013.01); *G02B 27/58* (2013.01); *G02F 1/011* (2013.01); *G02F 1/0136* (2013.01); *G02F 1/313* (2013.01); *G03H 1/0005* (2013.01); *G03H 1/2286* (2013.01); *G03H 1/2294* (2013.01); *H04B 10/2581* (2013.01); *G03H 2001/0434* (2013.01); *G03H 2001/0447* (2013.01)

(58) Field of Classification Search
  CPC ........ G02F 1/011; G02F 1/0136; G02F 1/313; G03H 1/0005; G03H 1/2286; G03H 1/2294; G03H 2001/0434; G03H 2001/0447; H04B 10/2581; H04N 1/40
  See application file for complete search history.

(56) References Cited

U.S. PATENT DOCUMENTS

| | | | | |
|---|---|---|---|---|
| 6,744,033 | B2* | 6/2004 | Ikeda | H04N 1/02815 250/208.1 |
| 7,194,155 | B1 | 3/2007 | Kahn et al. | |
| 8,743,352 | B2* | 6/2014 | Gong | G01N 15/1218 356/336 |
| 9,194,608 | B2* | 11/2015 | Lorenz | F24J 2/055 |
| 2002/0044279 | A1* | 4/2002 | Khoury | G01J 3/28 356/300 |
| 2004/0125380 | A1* | 7/2004 | Pepper | G01J 9/02 356/512 |
| 2004/0212799 | A1* | 10/2004 | Hell | G01N 21/6428 356/317 |
| 2010/0079753 | A1* | 4/2010 | Hehlen | G01J 3/02 356/301 |
| 2010/0220315 | A1* | 9/2010 | Morrell | G01N 15/1436 356/73 |
| 2011/0122416 | A1* | 5/2011 | Yang | A61B 5/0059 356/457 |
| 2011/0137126 | A1* | 6/2011 | French | A61B 1/00165 600/178 |
| 2012/0080611 | A1* | 4/2012 | Jones | G01J 1/0242 250/458.1 |
| 2013/0271592 | A1* | 10/2013 | Piestun | H04N 7/18 348/79 |

OTHER PUBLICATIONS

International Search Report and Written Opinionfor PCT/IB2013/052493, dated Oct. 28, 2013.
Cizmar, T. et al., Database Inspec [Online], The Institution of Electrical Engineers, Stevenage, (Sep. 26, 2011), "Shaping the light transmission through a multimode optical fibre: complex transformation analysis and applications in biophotonics", XP002705793, Database accession No. 12320328, & Optics Express Optical Society of America USA, vol. 19, No. 20, (Sep. 14, 2011), pp. 18871-18884.
Di Leonardo, R. et al., Database Inspec [Online], The Institution of Electrical Engineers. Stevenage.GB; (Jan. 2011), "Hologram transmission through multi-mode optical fibers", XP002705794, Database accession No. 11775938 & Optics Express Optical Society of America USA., vol • 19. No. 1, (Dec. 22, 2010), pp. 247-254.

* cited by examiner

METHODS AND APPARATUS FOR IMAGING WITH MULTIMODE OPTICAL FIBERS

This application is a national phase application of International application PCT/IB2013/052493, filed on Mar. 28, 2013, which designated the U.S. and claims priority to International Bureau Application No. PCT/IB2012/051509, filed on Mar. 29, 2012, the entire contents of each of which are hereby incorporated by reference.

FIELD OF THE INVENTION

The present invention relates to producing high-resolution images through a multimode fiber such as but not limited to endoscopic imaging. Embodiments of the present invention relate generally to imaging through multimode fibers, and in particular, to methods and apparatus for imaging through a multimode fiber. The illumination is delivered via a multimode fiber core and the optical information backscattered by a sample is collected and carried optically through the same said multimode fiber core prior to conversion to a digital image. After transmission of the scattered light through the multimode fiber, the digital image is formed by first converting the optical signal to an electronic signal by a single or multi-element photodetector and then by processing the said electronic signal. The multimode fiber imaging system may be passive, i.e., contain no active elements at the distal end of the multimode fiber or alternatively it may contain actuators/sensors at the distal end for certain uses. The formation of a digital image is achieved by:
  1. a wave front shaping method generating a known illumination pattern at the distal output (sample side) of a multimode fiber,
  2. changing the illumination pattern at the distal end of the fiber, collecting the backscattered response and converting it to electronic digital signal, and
  3. methods for extracting the information out of the said digital signal in order to form an image. The illumination pattern can be a diffraction limited spot or any other complex pattern that can be generated in either a deterministic or un-deterministic way.

The backscattered optical signal can be, but is not limited to, single or two photon fluorescence signal and/or Raman signal and/or linear backscattering intensity generated from a sample. Super-resolution, i.e., resolution below the diffraction limit, is achieved for example but not limited to, using the STimulated Emission Depletion microscopy (STED) technique or the Structured Illumination Microscopy (SIM) technique in combination with the MM fiber imaging method.

RELATED APPLICATION

This patent application claims priority to International application PCT/IB2012/051509 filed on Mar. 29, 2012 and incorporated by reference herein in its entirety.

BACKGROUND OF THE INVENTION

Optical endoscopes are shown to be devices of increasing interest for the investigation of the human body. State of the art endoscopes can be classified into two categories: wide-field endoscopes based on fiber bundles or GRIN lenses and scanning based systems using single mode optical fibers. In both cases, these systems are limited either by their size, flexibility, imaging resolution or their weak light collection. Most endoscopic systems are adapted from commonly used free space microscopy techniques where the image contrast can be generated in different ways.

An image can be, for example, obtained by collecting light scattered by a sample where the changes in the optical refraction index gives structural information. This linear scattering imaging can be improved by applying a specific illumination (as in bright-field or dark-field imaging). Biological structures can also naturally emit light by fluorescence when they absorb a probe light. By collecting the so-called auto-fluorescence signal, an image can be constructed. Artificial fluorescent markers can also be added to the sample for targeting a specific structure and obtain functional information about that structure. The fluorescence signal, emitted by these markers after excitation, can be collected to form what is called an optical fluorescence image.

Optical fluorescence imaging relies on a sample (dyed or not) emitting a fluorescence signal after light excitation. An image is obtained by collecting the fluorescence emission, which is usually at a longer wavelength than the excitation, either through a wide field microscope or a scanning optical microscope.

In wide field microscopy, the fluorescence image is directly collected and formed through the optical system. The endoscopic equivalent relies on the use of either a short (mm scale) small diameter GRIN lens as a microscope objective or fiber bundles, which consists of fibers arranged in an array. In the latter, the resolution is limited by the inter-core spacing.

Scanning optical microscopes, however, are based on producing an image point by point by scanning a diffraction limited focus spot. For each scanned position at the sample, the optical information, which can be either a linear signal (scattering, single fluorescence) or a non-linear signal, is collected to form an image. The detected light resulting from one illuminated volume element represents one pixel in the resulting image. The beam is scanned across the sample in two dimensions or in three dimensions (axially). For depth selectivity or sectioning, a pinhole can be added to form a confocal arrangement. In a confocal scanning microscope, the illumination/excitation beam first passes through an aperture and then is focused on the sample. Scattered and reflected laser light as well as any fluorescent light from the illuminated spot is then re-collected by the objective lens. The detection apparatus has a pinhole that obstructs the light that is not coming from the focal point. The out-of-focus light is rejected leading to a sharp-er image and giving the possibility to perform optical sectioning by acquiring images at various depths. A confocal arrangement can be made with GRIN-lens endoscopes but not with a fiber bundle.

Other imaging techniques based on non-linear effects are so-called two-photon imaging (or multi-photon imaging) and Raman imaging. In two-photon imaging, excitation is based on the effect that two photons of comparably lower energy than needed for one photon excitation, can also excite a fluorophore in one quantum event. Each photon carries approximately half the energy necessary to excite the molecule. An excitation results in the subsequent emission of a fluorescence photon. Since the probability of simultaneous absorption of two photons is extremely low, a concentrated flux of photons is necessary, a condition experimentally realized at the focus of a high numerical objective and using femtosecond pulsed laser sources. Two-photon imaging systems typically require fluorophores tagged to a specimen of interest in order to obtain strong two-photon efficiency. GRIN-lens endoscopes and fiber bundles have been demonstrated to provide dispersion compensation to maintain a short pulse duration at the sample.

Raman imaging uses the Raman effect which is an inelastic scattering effect in which a probe photon (from a probe beam) interacts with the vibrational levels of the probed molecules. The resulting scattered photon is energy-shifted by an amount equal to the energy of the vibrational level involved. Raman scattering is weak (typ. 1 ppm) and thus a high number of photons per volume is needed to produce a Raman shifted photon. This condition is experimentally realized at the focal spot of a lens. Continuous wave laser beams are typically used. An enhancement of the Raman signal is realized by a nano-patterned surface (metal) on which the probed molecules reside. The electric field at specific spots on the nano-patterned surface is enhanced by a plasmonic effect (electron resonance effect with the light frequency). The so-called surface enhanced Raman scattering (SERS) is proportional to the incident optical electric field to the power four at resonance. Both two-photon and Raman techniques are based on point-by-point measurements and thus a scanning system is required to form an image as in a scanning optical microscope.

In microscopy, the lateral spatial resolution d of a sample is limited by the wavelength of light λ, and the numerical aperture NA of the microscope objective via the Abbe relation: $d=\lambda/2NA$. A better resolution can be achieved if one uses a so-called "super-resolution" imaging microscopy technique. Two major techniques are used that both rely on a patterned illumination: STimulated Emission Depletion microscopy (STED) which is a scanning based method and Structured Illumination Microscopy (SIM), which is a widefield method.

STED (stimulated emission depletion) microscopy makes use of non-linear de-excitation of fluorophores to overcome the Abbe diffraction limit and was proposed by Hell and co-workers (U.S. Pat. Nos. 5,731,588, 7,064,824, 7,430,045). With this technique, a structure is tagged with a substance such as a fluorophore that can be in either of two states having each a specific optical property. The state of the substance can be toggled between the first and second state and vice-versa by means of a switch-over optical signal. The light induced toggling between the two states is non-linear with light intensity. A first excitation beam is focused by a high numerical aperture objective lens on the sample tagged with the fluorophores to bring the latter to an excited state. A second beam, red-shifted to the first optical beam is focused by the same objective to form a doughnut beam at its focus. The red-shifted beam toggles the fluorophores to a second state by a stimulated depletion effect. The doughnut beam has zero intensity only at the center and thus fluorophores, located within an area smaller than the diffraction limit around the center, remain in the first state. Fluorophores in the first state emit a fluorescence radiation that is collected by the same high numerical objective and separated by color filters from the first and second excitation/de-excitation beams respectively. To form an image, the Gaussian and doughnut spot size are scanned together, e.g., by a system of rotating mirrors placed before the high numerical objective. The lateral spatial resolution d in STED is dependent on the light intensity of the de-excitation beam $I_{STED}$: $d=1/NA*sqrt(1+I_{STED}/I_{sat})$.

SIM microscopy is, unlike STED microscopy, a widefield technique that can improve the resolution of a fluorescence light microscope by at least a factor of two (U.S. Pat. No. 6,239,909; US 2012/0026311). SIM uses a grid to create several interference patterns on the sample. The illumination pattern interacts with the fluorescent probes in the sample to generate interference patterns known as moiré fringes that include high-resolution information that is normally inaccessible. These moiré patterns are superimposed upon each other to form a single image. This can be done by using widefield microscopy and placing a fine mesh grating in the light path before excitation. In Fourier optics, the resolution limit is defined by the optical transfer function, which is the normalized Fourier transform of the point-spread function. When two frequencies are mixed (the multiplication of two signal), moiré fringes are created. When moiré patterns are combined, information outside of the conventionally observable space becomes observable.

Other super resolution microscopy techniques are based on a stochastic illumination, as in PALM (Photo Activated Localization Microscopy) and STORM (Stochastic Optical Reconstruction Microscopy). They utilize sequential activation and time-resolved localization of photoswitchable fluorophores to create high-resolution images. During imaging, only an optically resolvable subset of fluorophores is activated to a fluorescent state at any given moment, such that the position of each fluorophore can be determined with high precision by finding the centroid position of the single-molecule images of particular fluorophore. The fluorophore is subsequently deactivated, and another subset is activated and imaged. Iteration of this process allows numerous fluorophores to be localized and a super-resolution image to be constructed from the image data.

The microscopy techniques mentioned above rely on free-space optical components such as high numerical aperture microscope objectives and can be adapted, in a more or less straightforward way, to an endoscopic device. Scanning-based endoscopic devices usually rely on the use of a single-mode fiber for the focused excitation and a second fiber, usually multimode, for light collection. In the case of the wide field technique, GRIN rigid lenses are used or bundles of large number of single-mode fibers are used, even if they have an inherent resolution limitation coming from the inter core spacing.

With respect to super-solution techniques, STED, PALM and STORM have never been implemented in an endoscopic device but SIM has already been implemented using a fiber bundle.

In Raman imaging, fiber probes exist in which the probe beam is transmitted to the sample under test by a single mode fiber (U.S. Pat. No. 5,112,127). Because of the tight light confinement in the single mode core of the fiber, a strong Raman signal is generated in the fiber itself. To mitigate this effect, a larger core fiber is used. However, this is achieved at the expense of resolution. This Raman signal needs to be optically removed from the main beam as this Raman signal (elastically scattered by the sample) can mask the Raman signal generated by the sample. Because of this Raman induced signal in the fiber, a small lens is placed at the distal end of the fiber to collimate the beam. A narrow bandpass filter is placed in the path of the collimated beam to block the Raman signal and to transmit only the probe beam. A high pass filter then reflects the probe beam. A second lens focuses the probe beam onto the sample. In the return path, a notch filter is placed behind the high pass filter to block the Rayleigh scattered probe beam while transmitting the frequency shifted Raman signal. The Raman signal is then focused in a multimode fiber for collection. The diameter of the fiber probe is thus of the order of 10 mm to accommodate the free-space collimating lenses and filters.

Multimode fibers present many advantages for light transmission such as a large fiber core and a large numerical aperture, which lead to a high fiber coupling efficiency and high light gathering feature. For their light high collection efficiency, they are already used for image collection in endoscopy. However, light propagation through a multimode fiber produces a speckle pattern and thus a specific spatial excitation/illumination through a MM fiber is a challenge. Indeed, as the optical field is coupled into the fiber, it excites different fibers modes which propagate along the fiber, possibly exchanging energy between them through the mechanisms of intermodal coupling and finally reaching the output fiber surface where they interfere; generating what is seemingly a random speckle pattern. Multimode fibers have a number of modes M given by $M=4V2/p2$ f, for $M\gg1$ where $V=p\cdot f\cdot NA/l$. l is the wavelength of the light, NA is the numerical aperture of the multimode fiber and f is the fiber core diameter. By way of example, a multimode fiber with core diameter 200 mm, NA=0.42 and wavelength 532 nm possess 100,000 modes. A single mode fiber has only 1 mode (M=1).

In addition to this modal spatial scrambling, dispersion effects are also very important in multimode fibers resulting in a temporal spreading of an input light pulse. These two aspects have always limited their use for light transmission, and particularly for fiber-based imaging.

Light scrambling occurring in multimode fibers produce speckle patterns that are similar to light patterns created as a result of propagation in a diffuse medium. There are major differences between propagation in a diffuse medium and in a multimode fiber. One of them, is the forward-only propagation in multimode fiber whereas backward scattering occurs in a diffuse (turbid) medium. Digital phase conjugation methods have been shown to suppress turbidity in a turbid medium: U.S. Pat. No. 5,378,888 (HOLOGRAPHIC SYSTEM FOR INTERACTIVE TARGET ACQUISITION AND TRACKING), US patent application 2011/0122416 A1 (TURBIDITY SUPPRESSION BY OPTICAL PHASE CONJUGATION USING A SPATIAL LIGHT MODULATOR) and publication by C.-L. Hsieh, Y. Pu, R. Grange, and D. Psaltis, "Digital phase conjugation of second harmonic radiation emitted by nanoparticles in turbid media," Opt. Express 18, 12283-12290, 2010.

A digital phase conjugation technique has been applied to a bundle of near single mode fibers to coherently combine the output of 3 fibers: C. Bellanger, A. Brignon, J. Colineau, and J. P. Huignard, "Coherent fiber combining by digital holography," Opt. Lett., OL 33, 2937, 2008. The same technique was applied to a fiber with a low number of modes (M=4): M. Paurisse, M. Hanna, F. Druon, P. Georges, C. Bellanger, A. Brignon, and J. P. Huignard, "Phase and amplitude control of a multimode LMA fiber beam by use of digital holography," Opt. Express 17, 13000-13008, 2009). However such a technique has not been shown to work with very high number of modes. There is thus a need to develop a technique for a very high number of modes. This patent describes a method to use digital phase conjugation for a very high number of modes. Digital phase conjugation is a "single shot" technique meaning that only one digital hologram suffices to control the wavefront to achieve a desired output.

Other techniques are iterative, meaning that the wavefront is optimized sequentially to maximize the response of a beacon (e.g. single detector, fluorescent particle) placed at the output of the multimode fiber. Such iterative techniques applied to multimode fibers are described in Di Leonardo et al. (R. Di Leonardo and S. Bianchi, "Hologram transmission through multi-mode optical fibers," Opt. Express 19, 247-254, 2011) and T. Čižmár and K. Dholakia, "Shaping the light transmission through a multimode optical fibre: complex transformation analysis and applications in biophotonics," Opt. Express 19, 18871, 2011.

Yet another method of sending a desired pattern through a turbid medium or multimode fiber is to calibrate the medium i.e. determining the transmission matrix T such that an input image x is transformed into an output image y by the linear relation y=T*x. S. M Popoff, G. Lerosey, R. Carminati, M. Fink, A. C Boccara and S. Gigan et al. "Measuring the Transmission Matrix in Optics: An Approach to the Study and Control of Light Propagation in Disordered Media", PRL 104, 2010 describes such a method to measure the transmission matrix T.

SUMMARY OF THE INVENTION

This present invention is a method and apparatus to form high-resolution images from a multimode fiber in a lens-less manner. A wavefront shaping method such as Digital Phase Conjugation (DPC) technique is used to control light transmission through a multimode fiber both for excitation and collection. Other wavefront shaping methods are also described to achieve the same goal, i.e. illuminating a sample with a chosen pattern through a MM fiber and recovering the information from light collected back through the MM fiber. In this way, an apparatus is proposed to generate a desired light pattern at the distal end of a multimode fiber or array of multimode fiber also called fiber bundle in the text. These patterns include, and are not limited to, a diffraction limited spot, a doughnut pattern as used for STED, a moiré pattern as used for SIM or any other deterministic or random pattern. In a scanning based system, the image is formed pixel by pixel. In a wide field system, the image is recovered from a collection of random patterns with or without a stochastic illumination as in PALM and STORM. Methods and apparatus are described to compensate for the deleterious effects caused by fiber bending or other environmental perturbations.

In a separate embodiment, the present invention discloses means and methods to transmit high-speed digital information in a multimode fiber.

In a first aspect the invention provides a method for deterministic light transmission through a multimode waveguide comprising the steps of providing the multimode waveguide, calibrating the multimode waveguide, whereby the calibrating comprises coupling in light at an input side of the multimode waveguide, and analyzing light coupled in at the input side of the multimode waveguide, at an output side of the multimode waveguide. The method for deterministic light transmission further comprises conditioning the output of the multimode waveguide by controlling a spatial light modulator to choose an appropriate light field at the proximal tip of the multimode waveguide.

In a first preferred embodiment the output side of the multimode waveguide is an opposite end of the multimode waveguide to the input side or the same side as the input side.

In a second preferred embodiment the step of calibrating is realized through digital phase conjugation.

In a third preferred embodiment the step of calibrating is realized through transmission matrix measurement.

In a fourth preferred embodiment, the step of calibrating is realized through iterative wave-front control.

In a fifth preferred embodiment the method further comprises adjusting a focal spot at the output side of the multimode waveguide by digitally controlling the spatial light modulator in the conditioning step, directing the focal spot exiting the output side of the multimode waveguide to a sample, and illuminating the sample by scanning the focal spot on the sample.

In a sixth preferred embodiment the method further comprises collecting light arriving from the sample as a result of illuminating, at the output side of the multimode waveguide, sampling the collected light for determined scanning positions, whereby each determined scanning position represents a pixel, and constructing an image of the sample pixel by pixel, the pixels corresponding to the collected light at each determined scanning position.

In a seventh preferred embodiment the method further comprises steps of directing light to a sample, analyzing scrambled light collected through the multimode waveguide from a sample to recover an image, analyzing light collected from the sample to extract axial information, and constructing an image of the sample in three dimensions, the axial dimension corresponding to different depths in the sample.

In an eighth preferred embodiment the method further comprises steps of providing light pulses at the step of coupling in light, and providing short light pulses at the output side of the multimode waveguide by applying an appropriate light field at the step of conditioning the waveguide when controlling the spatial light modulator.

In a ninth preferred embodiment the method further comprises steps of determining a wavelength required for excitation of the sample, and choosing a wavelength twice the wavelength required for excitation of the sample for the light at the step of providing light pulses.

In a tenth preferred embodiment the method further comprises steps of placing a scattering medium at the output side of the multimode waveguide to decrease the size of the focal spot on the sample, choosing a size of the focal spot at the output side of the multimode waveguide, and choosing a position of the focal spot at the output side of the multimode waveguide.

In an eleventh preferred embodiment the multimode waveguide is a rigid waveguide, and the method further comprises positioning the distal tip of the multimode waveguide on a surface of a sample.

In a twelfth preferred embodiment the multimode waveguide is a flexible waveguide, and the method further comprises inserting the multimode waveguide in a sample and moving the multimode waveguide while adapting the conditioning pattern in the step of conditioning the output.

In a thirteenth preferred embodiment the method further comprises achieving super-resolution by projecting determined spatial patterns at the step of conditioning the waveguide.

In a fourteenth preferred embodiment the method further comprises achieving super-resolution by exciting the sample with a first wavelength and depleting with a second wavelength with a determined ring pattern.

In a fifteenth preferred embodiment the method further comprises achieving super-resolution by stochastically illuminating the sample when directing light from the output side of the waveguide.

In a sixteenth preferred embodiment the method further comprises calibrating the multimode waveguide from the same side as the input side in real-time at the step of calibrating the multimode waveguide.

In seventeenth preferred embodiment the method further comprises controlling the polarization of light at the output side of the multimode waveguide, analyzing light coupled in at the input side of the waveguide, at an output side for all the polarizations, and conditioning the output of the multimode waveguide for all the polarizations.

In an eighteenth preferred embodiment the method further comprises transmitting high-speed digital information.

In a nineteenth preferred embodiment the multimode waveguide is an optical waveguide that presents modal scrambling and high dispersion, wherein the multimode waveguide is one of items in the following list:
   i. a step-index fiber,
   ii. a graded index fiber,
   iii. a double-clad fiber,
   iv. a large mode area fiber,
   v. a fiber bundle,
   vi. a no-core fiber, and
   vii. a rod.

In a twentieth preferred embodiment the method further comprises providing a beacon means whereby the step of coupling comprises coupling light from the beacon means.

In a second aspect the invention provides a system for deterministic light transmission through a multimode waveguide. The system comprises the multimode waveguide, calibrating means configured for calibrating the multimode waveguide, whereby the calibrating means comprises light coupling means for coupling light at an input side of the multimode waveguide, and analyzing means arranged for analyzing light at an output side of the multimode waveguide. The analyzing means comprises a digital analyzing system that digitally analyzes a complex light field in its phase or amplitude properties. The system for deterministic light transmission further comprises conditioning means configured to condition the output of the multimode waveguide, whereby the conditioning means comprises a spatial light modulator configured to choose the appropriate light field at the proximal tip of the multimode waveguide.

In a twenty-first preferred embodiment the multimode waveguide is an optical waveguide that presents modal scrambling and high dispersion, wherein the multimode waveguide is one of items in the following list:
   i. a step-index fiber,
   ii. a graded index fiber,
   iii. a double-clad fiber,
   iv. a large mode area fiber,
   v. a fiber bundle,
   vi. a no-core fiber, and
   vii. a rod.

In a twenty-second preferred embodiment the spatial light modulator is one of items of the following list:
   i. a phase liquid crystal spatial light modulator,
   ii. a deformable mirror,
   iii. a binary amplitude modulator, and
   iv. an analog amplitude modulator.

In a twenty-third preferred embodiment the output side of the multimode waveguide is either
   i. an opposite end of the waveguide to the input side, or
   ii. the same side as the input side.

In a twenty-fourth preferred embodiment the digital analyzing system comprises a coherent holographic system.

In a twenty-fifth preferred embodiment the digital analyzing system comprises an incoherent system.

In a twenty-sixth preferred embodiment the conditioning means are further configured to adjust a focal spot at the output side of the multimode waveguide by digital control of the spatial light modulator. The system further comprises directing means configured to direct the focal spot exiting the output side of the multimode waveguide to a sample, and scanning means configured to illuminate the sample by scanning the focal spot on the sample.

In a twenty-seventh preferred embodiment the system further comprises collecting means configured to collect light arriving from the sample as a result of illuminating, at the output side of the multimode waveguide, sampling means configured to sample the collected light for determined scanning positions, whereby each determined scanning position represents a pixel, and image constructing means configured to construct an image of the sample pixel by pixel, the pixels corresponding to the collected light at each determined scanning position.

In a twenty-eighth preferred embodiment the system further comprises an appropriate filter configured to separate light collected from the sample from excitation light by directing the light arriving from the sample.

In a twenty-ninth preferred embodiment the system further comprises a spectrometer, and directing means configured to direct Raman light arriving from the sample to the spectrometer.

In a thirtieth preferred embodiment the system further comprises beacon means configured to calibrate the multimode waveguide from the same side as the input side in real-time. The beacon means comprises a beacon light source arranged such that light from the beacon light source is coupled by the light coupling means.

In a thirty-first preferred embodiment the beacon light source is one of
a focus spot generated by an objective lens,
a specified light pattern,
multiple foci spots, and
a virtual beacon light source generated by a device at the distal end of the multimode fiber.

In a thirty-second preferred embodiment the system further comprises means for generating the virtual beacon light source, comprising excitation means for providing excitation light from the same side as the input side of the multimode waveguide, and second analyzing means at the input side of the multimode waveguide for recording the light pattern generated by the beacon light source after propagating through the multimode waveguide.

In a thirty-third preferred embodiment the excitation means are provided by one of
a co-propagating single mode fiber,
a plurality of co-propagating single mode fibers, and
a co-propagating single mode core in a double-clad multimode waveguide.

In a thirty-fourth preferred embodiment the device is one of the items of the following list:
micro-lens; and
a hologram.

In a thirty-fifth preferred embodiment the system further comprises means configured to compare the analyzed light pattern with a database of light patterns corresponding to different configurations of the multimode waveguide.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DETAILED DESCRIPTION OF THE INVENTION

Figure 1:
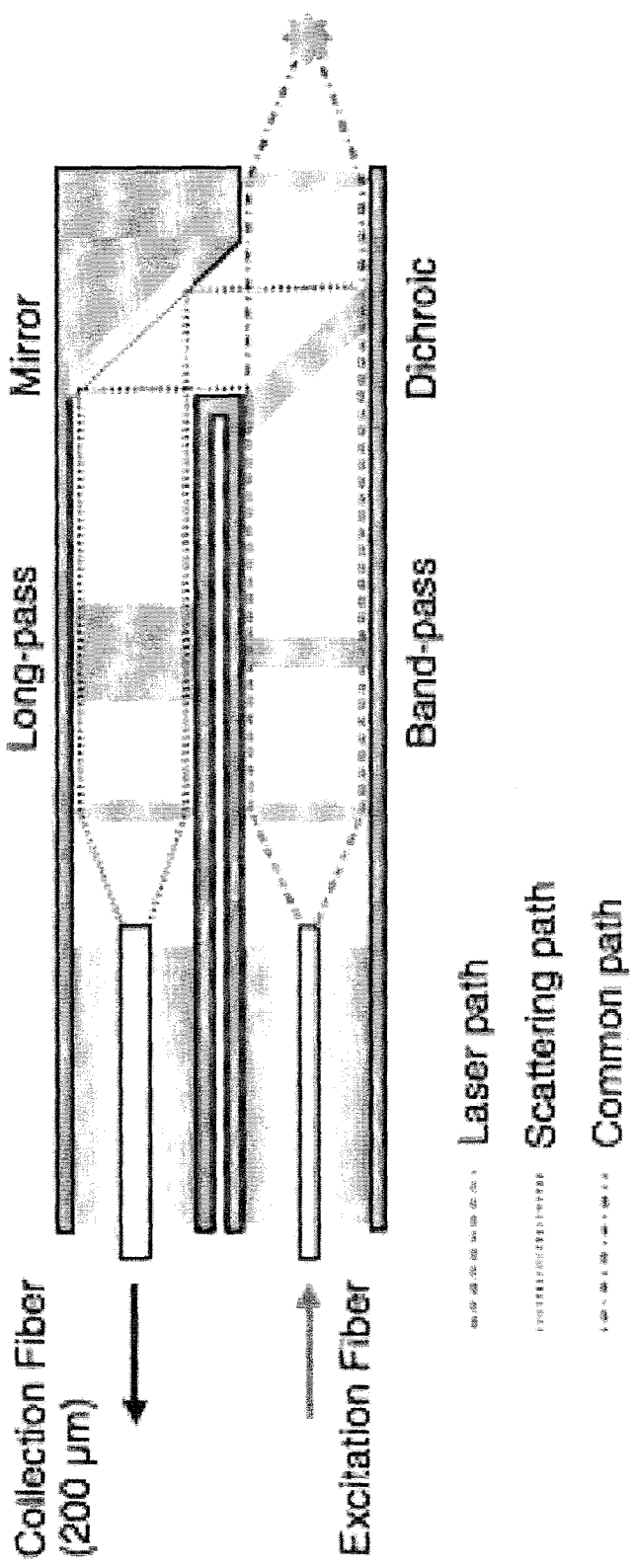
FIG. 1 (prior art) shows a Raman fiber probe.

In the following description, reference is made to the accompanying drawings, which form a part hereof, and in which are shown, by way of illustration, several embodiments of the present invention. It is understood that other embodiments may be utilized and structural changes may be made without departing from the scope of the present invention. In the text, the use of the term multimode fibers comprises any multimode waveguide element.

The lensless multimode fiber based imaging system and apparatus allows for several embodiments including 1) a system for delivering a sequence of complex illumination patterns such as, but not limited to a diffraction limited spot at the distal end of a MM fiber and/or 2) a system for collecting scattered light and constructing an image through a multimode fiber and/or 3) a system for performing non-linear imaging through a multimode fiber such as but not limited to, Raman and two photon and/or 4) a system to achieve super-resolution imaging through a multimode fiber based on a specific illumination pattern and/or 5) a system that allows for the control of the field of view, working distance and resolution.

In at least one embodiment, the present invention relates to a system and method for deterministic light transmission through a multimode fiber. The system first contains a multimode fiber including, but not limited to, step-index fiber, graded index fiber, double-clad fiber, large mode area fiber, fiber bundles, any optical waveguide that presents modal scrambling and high dispersion and no-core fibers such as but not limited to rods. In a first step, the multimode fiber is calibrated, i.e. that light coupled in at one side of the fiber is analyzed at the output of the fiber, which can be the opposite end of the fiber or it can be the same side that light was coupled in. This calibration is based on a system that digitally analyzes the complex light field (phase and amplitude) including, but not limited to, a coherent holographic system and/or an incoherent system for which phase and amplitude is recovered via a method such as, but not limited to Transport of Intensity (TIE) for wavefront analysis. Calibration methods, include, but are not limited to, digital phase conjugation, transmission matrix measurement and iterative wavefront control. The modulation of the input field is performed with a spatial light modulator (SLM) such as, but not limited to, phase liquid crystal SLMs, deformable mirrors, binary or analog amplitude modulators. In a second step, once the multimode fiber is calibrated, the system conditions the output of the multimode fiber by choosing the appropriate light field at the proximal tip of the multimode fiber by way of a spatial light modulator. The output pattern includes, but is not limited to, a diffraction limited focus spot. Aberrations, modal scrambling and dispersion are compensated for, so that the spatial properties of the light at the distal end of the fiber are controlled.

In at least one embodiment, the system allows for scanning a diffraction-limited spot at the distal end of the fiber by sending the appropriate light fields at the proximal end. Focusing at the fiber tip does not require a lens and scanning the focal spot does not require mechanical actuators, rather this is obtained purely by digital control of the spatial light modulator. In another embodiment, the portion of the endoscope from the proximal end to the distal end is passive i.e. does not contain active elements such as electrical or magnetic actuator. In this embodiment the endoscope is digitally controlled to provide a scanning lensless endoscope.

In at least one embodiment, the system allows for light collection with the same multimode fiber. Indeed, multimode fibers present large light gathering capabilities due to their large core and numerical aperture. Based on the scanning system described above, the multimode fiber is used for signal collection whereby, for each scanned position of a sample the signal is collected. The beam is scanned point by point at the distal end of the multimode fiber. Light collected for one scanning position represents one pixel in the resulting image. The image is constructed pixel by pixel. The number of scanning points gives the number of pixels in the image and the lateral image resolution is given by the maximum of the distance between two neighboring scanning points and the focal spot size.

In one embodiment, light collected from the fiber is generated by, but not limited to, linear scattering, single fluorescence of the sample or of a dye attached to a specific structure of the sample or a non-linear signal generated by coherent or non coherent processes such as but not limited to second harmonic generation and multi-photon excitation respectively. The system comprises then a dichroic beam splitter allowing for the separation of the excitation light injected at the proximal end of the fiber and the fluorescence light collected through the fiber, which is at longer wavelength. A specific filter should be used in front of the detector in order to reject the background signal generated at the excitation wavelength.

In one embodiment, light collected from the fiber is directed, via an appropriate beam splitter to a Raman spectrometer. The Raman spectrum is then measured with, but not limited to, a dispersive monochromator or a Fourier based interferometer. Since spontaneous Raman scattering is weak (~1 ppm), high selectivity filters need to be used in order to separate the inelastically scattered light from the intense Rayleigh scattered laser light. The Raman signal collection combined with the scanning capability of the system allow for the construction of Raman images with chemical specificity. Because the probe beam is delivered by a large core multimode fiber, the non-linear signal, such as but not limited to Raman, generated by the fiber itself can be neglected compared to the non-linear signal produced by the sample under test at the focal point. Sapphire fibers have low fluorescence and Raman scattering compared with silica fibers and are preferred as such. One or more multimode fibers, surrounding the multimode fiber bringing the probe beam are also disclosed to collect the Raman signal. In yet another embodiment, the multimode fiber bringing the probe beam is also the collecting fiber for the non-linear signal such as but not limited to Raman.

In one embodiment, the invention allows for axial depth sectioning in an image. A database of speckle patterns is recorded corresponding to an ensemble of scattered point sources distributed in the field of view of the multimode fiber. Later, a 3-dimensional sample is illuminated through the output of the multimode fiber, which can be for example, but not limited to, a plane wave. The resulting scattered speckle image is captured and correlated with the speckle patterns of the database. A 3-dimensional image is then constructed by assigning the value of the correlation for each spatial location of the known reference patterns.

Other embodiments disclose a temporal pulse shaping system in order to deliver short light pulses through the fiber. This temporal pulse shaping can be a separate apparatus combined with the above-mentioned wavefront shaping system or only one system allowing for both temporally and spatially shaping the beam. The ability to control light propagation through a multimode fiber both in space and time enables illuminating the sample with a short pulse in the desired spatial pattern, including but not limited to a single focus spot or a doughnut beam. A temporally short light pulse spatially focused will generate a non-linear signal in the sample, such as but not limited to a two photon signal. In this case, the excitation wavelength is twice the wavelength of the two photon signal, and by choosing the excitation to lie in the so-called therapeutic window (approximately 600-800 nm), the penetration depth is increased in the sample and enables a better out-of-plane light rejection.

In one embodiment, the resolution of the endoscope system is increased by placing a scattering medium at the distal end of the multimode fiber, which has for effect to increase the effective numerical aperture of the fiber. Propagation of light through this scattering medium is controlled in the same way as in the fiber: the ensemble multimode fiber and scattering medium constituting the new complex medium through which light is spatially and temporally controlled. A potential difficulty arising from the suggested geometry is the fact that the scattering phenomena both during focusing and also during light collection for imaging are going to decrease the expected photon budget. This can be overcome by just increasing the power of the excitation laser source or by using a less scattering medium. A different approach could be to use a notch filter with an annular scattering ring in a dark-field configuration. This approach will exploit the annular ring for the generation of the focused spot and on the collection part; most of the fluorescent light will propagate backwards unaffected into the fiber.

Further, in at least one embodiment, the wavefront shaping system allows for a controlled patterned illumination of a sample. By choosing the right phase pattern to project at the proximal end of the multimode fiber, the system generates a specific light pattern at the distal end, including but not limited to, a doughnut shaped beam, or a sinusoidal light illumination, or Hadamard matrix based illumination.

Additionally, in at least one embodiment, the calibration method allows also for image recovery from the scrambled light collected at the proximal end of the multimode fiber. This capability allows for wide field imaging through the multimode fiber where the image is reconstructed from the speckle. A calibration of the fiber can be provided from one side of the fiber by partially reflecting the speckle field at the distal end of the multimode fiber and by changing the incidence angle of the reference beam.

Based on the wide field imaging capability and the patterned illumination capability mentioned above, one embodiment discloses a SIM (structured illumination microscopy) system. In the SIM system, super solution imaging is achieved by illuminating the sample with different light patterns that incorporate higher spatial frequencies. In the SIM embodiment of the multimode waveguide based endoscopic apparatus, the sample is illuminated with different patterns from the multimode waveguide. The signal reflected by the sample is transmitted back through the multimode waveguide and unscrambled thanks to the image recovery embodiment described above.

Another embodiment discloses a super-resolution imaging capability based on stochastic illumination as in PALM (Photo Activated Localization Microscopy) or STORM (Stochastic Optical Reconstruction Microscopy). Based on the image recovery ability described above, advantage can be taken from a stochastic illumination to extract, from the image transmitted through the multimode waveguide, the position of each single emitter in a sample. The iteration of the process allows constructing a super-resolution image.

Other embodiments disclose a beacon beam providing a reference virtual focal point source at the distal end of the MM fiber. The conformation of the fiber (bending, temperature, strain) modifies the distribution of the modes inside the MM fiber, but does not modify the reference virtual point source. Thus this virtual point source provides a reference that is used to continuously calibrate the system i.e the distribution of modes. In one embodiment this beacon beam serves as a sensing beam because the scrambled light pattern generated by this beam at the proximal end gives information about the fiber conformation, for example but not limited to a bending configuration. In one embodiment, the beacon source is a real optical source such as a point source of light, or a specified light pattern that can be excited in transmission or reflection. This includes, but is not limited to, a generated focus spot, a generated optical pattern, multiple foci spots, coherent emitters, a reflection or scattering from a surface, an image.

In one embodiment, one or many single mode fibers co-propagates with the multimode fiber to illuminate an optical element near the tip of the multimode fiber to produce one or more virtual beacon beams, Gaussian or/and doughnut shaped but not limited to them. The optical element includes but is not limited to a lens, a hologram or a prism. These beacon beams back-propagate in the multimode fiber (from the distal to the proximal end) and interfere with a coherent reference beam to generate an interference pattern onto a digital camera at the proximal end of the multimode fiber. In another embodiment, a phase pattern is extracted from the said interference pattern. The said phase pattern is then fed to the beam shaping apparatus that provides the appropriate pattern at the proximal end of the multimode fiber so as to generate after propagation, the desired illumination, for example, but not limited to, a focused beam. In another embodiment, a set of interference patterns obtained as described above for different fiber bending configurations is stored into a database. By calibrating the fiber for each said bending configurations, either by using the phase conjugation technique (calibration point by point) or by determining the transmission matrix of the fiber, the bending configuration can be inferred by matching the interference pattern generated by the beacon with the patterns stored in a database. In these beacon embodiments, the system can achieve a real-time wavefront compensation of modal scrambling in the multimode fiber. In yet another embodiments, an array of beacons, as described above, each corresponding to a fiber in a fiber bundle is disclosed.

In yet at least another embodiment, the size of the focus spot, the distance from the fiber tip and also the number of focus spots can be controlled allowing for a lensless fiber endoscope with a flexible resolution, field of view and working distance. All these parameters are limited by the optical properties of the fiber or the complex medium (if the multimode fiber is combined to a scattering medium for higher resolution).

In yet another embodiment, a scattering element is created on the surface of the multimode fiber core to couple light out to the side of the fiber. This allows for creating patterns along and around the side of the fiber thus expanding the field of view of the endoscope. In another embodiment, a scattering rod is fused to the core of the multimode fiber. In another embodiment, structures inside the multimode fiber, such as but not limited to slanted gratings, deflect light to the side of the fiber.

In a separate embodiment, the present invention discloses means and methods to transmit high speed digital information in a multimode fiber. By calibrating the multimode fiber, the input output relationship is known and thus an array of two dimensional optical sources (data) can be mapped onto a 2-dimensional array of detectors at the distal end of the fiber.

FIG. 1 (State of the Art) is a drawing of a Raman probe. At the distal end of the single mode fiber, a small lens collimates the beam and a transmission narrowband filter blocks the Raman signal and transmits the probe beam. A high pass filter reflects the probe beam, which is then focused on the sample under test by a second lens. A notch filter placed behind the high pass filter blocks the Rayleigh scattered probe beam. The filtered Raman signal is then focused in a multimode fiber for collection. The diameter of the fiber probe is thus of the order of 10 mm to accommodate the free space collimating lenses and filters.

Figure 2:
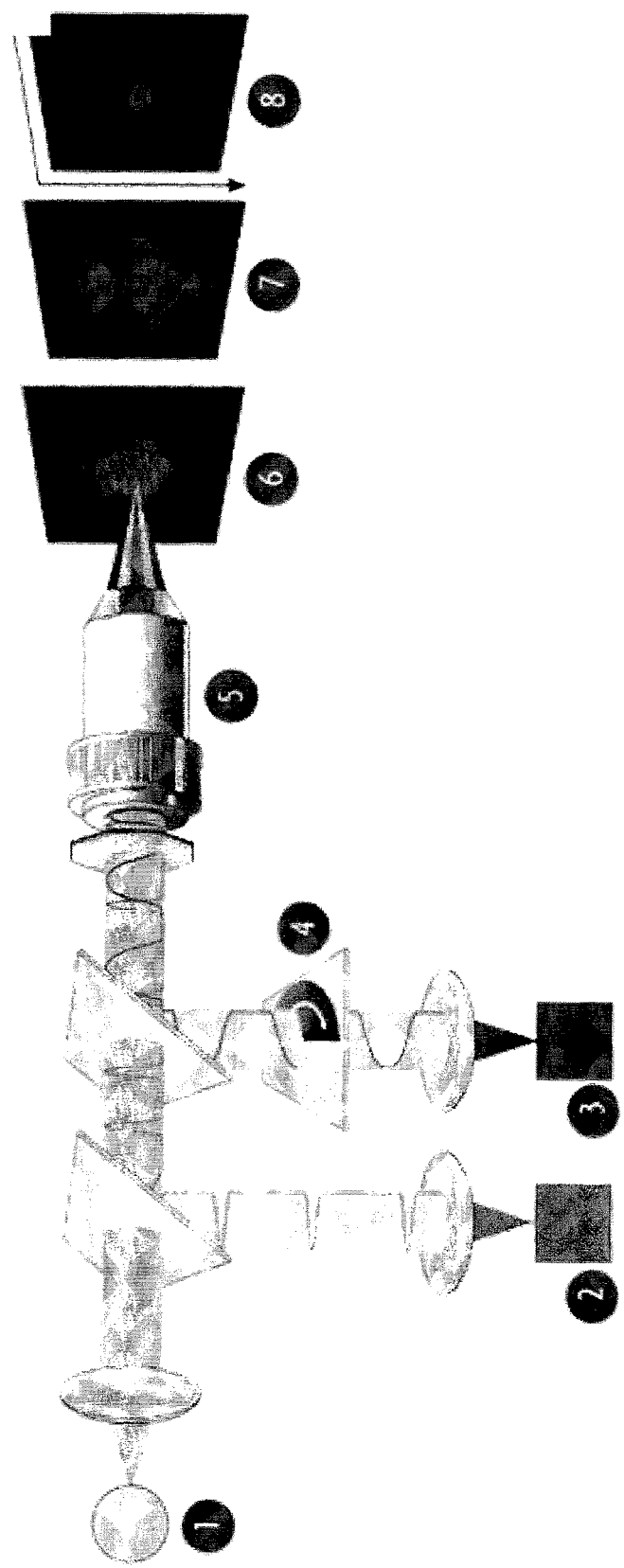
FIG. 2 (prior art) shows a set-up for stimulated emission depletion microscopy (STED).

FIG. 2 describes the principle of STED (Stimulated Emission Depletion) microscopy. A first excitation beam is focused by a high numerical aperture objective lens on the sample tagged with the fluorophores to bring the latter to an excited state. A second beam, red-shifted, is focused by the same objective to form a doughnut beam. The red-shifted beam toggles the fluorophores to a second state by a stimulated depletion effect. The doughnut beam has zero intensity only at the center and thus fluorophores, located within an area smaller than the diffraction limit around the center, remain in the first state. Fluorophores in the first state emit a fluorescence radiation that is collected by the same high numerical objective and separated by color filters from the first and second excitation/de-excitation beams respectively.

Figure 3:
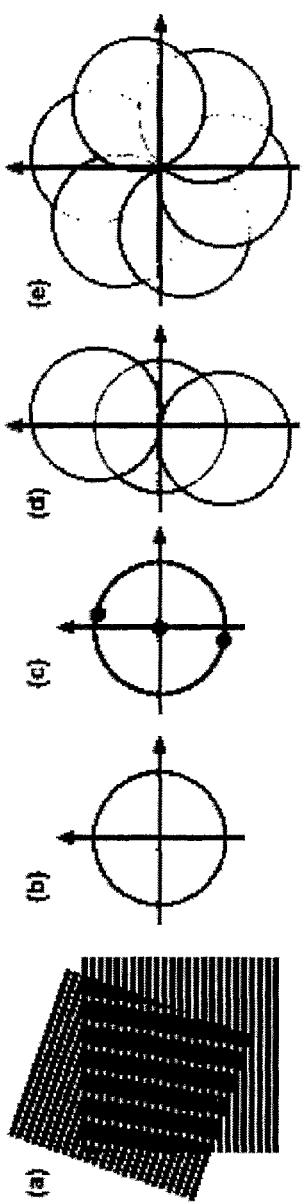
FIG. 3 (prior art) shows the principle of structured illumination microscopy.

FIG. 3 describes the principle of resolution enhancement by structured illumination. FIG. 3a is an example of two superimposed sinusoidal illumination patterns creating a Moiré pattern. FIG. 3b shows the region in frequency space that is observable by conventional microscopy. FIG. 3c shows that each sinusoidal illumination pattern has three frequency components: one at the origin representing the average intensity, and two at ±k1, representing the modulation. FIG. 3d shows the observable region for conventional microscopy in the center and the extended region due to structured illumination. Centered on ±k1, a new set of information becomes visible. FIG. 3e shows the corresponding observable regions if the procedure is repeated with other pattern orientations. The much larger region of observable spatial frequencies (e) compared with that shown in (b) makes it possible to reconstruct the sample with correspondingly increased spatial resolution.

Figure 4:
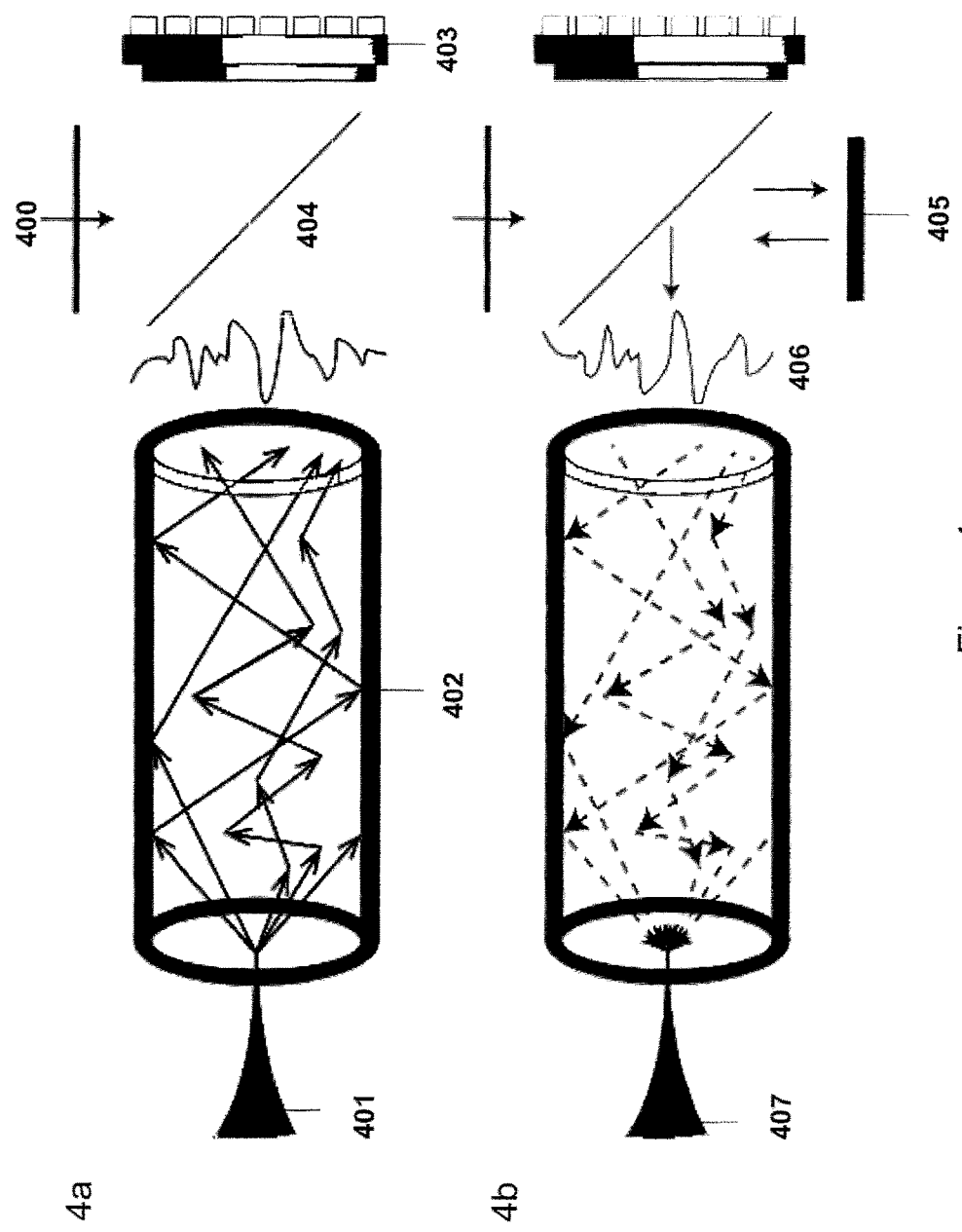
FIG. 4 shows the principle of digital phase conjugation in a multimode waveguide.

FIG. 4 shows the principles of focusing through a multimode fiber by digital phase conjugation. In a first calibration step (FIG. 4a), a focused calibration beam 401 is injected at one end of the multimode fiber 402. The beam coming out the other end of the multimode fiber 402 is combined, via beam-splitter 404, with a coherent reference beam 400 with a small angle. The resulting off-axis interferogram is recorded on a two dimensional detector 403. In a second reconstruction step (FIG. 4b), the phase extracted form the said off-axis interferogram is displayed onto spatial light modulator 405. Reference beam 400 is incident and diffracted by said spatial light modulator 405. The diffracted beam 406 is reflected by beam-splitter 404 and backward propagated through the fiber 402. A tightly focused spot 407 is then observed at the distal end of the fiber. The beam-splitter 404 can be a thick volume reflection holographic filter that transmits the reference beam 400 and reflects the diffracted beam 406 because the angle of the diffracted beam is Bragg matched. A thick reflection holographic filter (millimeters) is known to be highly angularly selective, although efficient at the Bragg matching angle (see J. Goodman "introduction to Fourier Optics", Wiley). Beam-splitter 404 can also be a narrow band thin film interference filter or any filter with a high angular selectivity.

Figure 5:
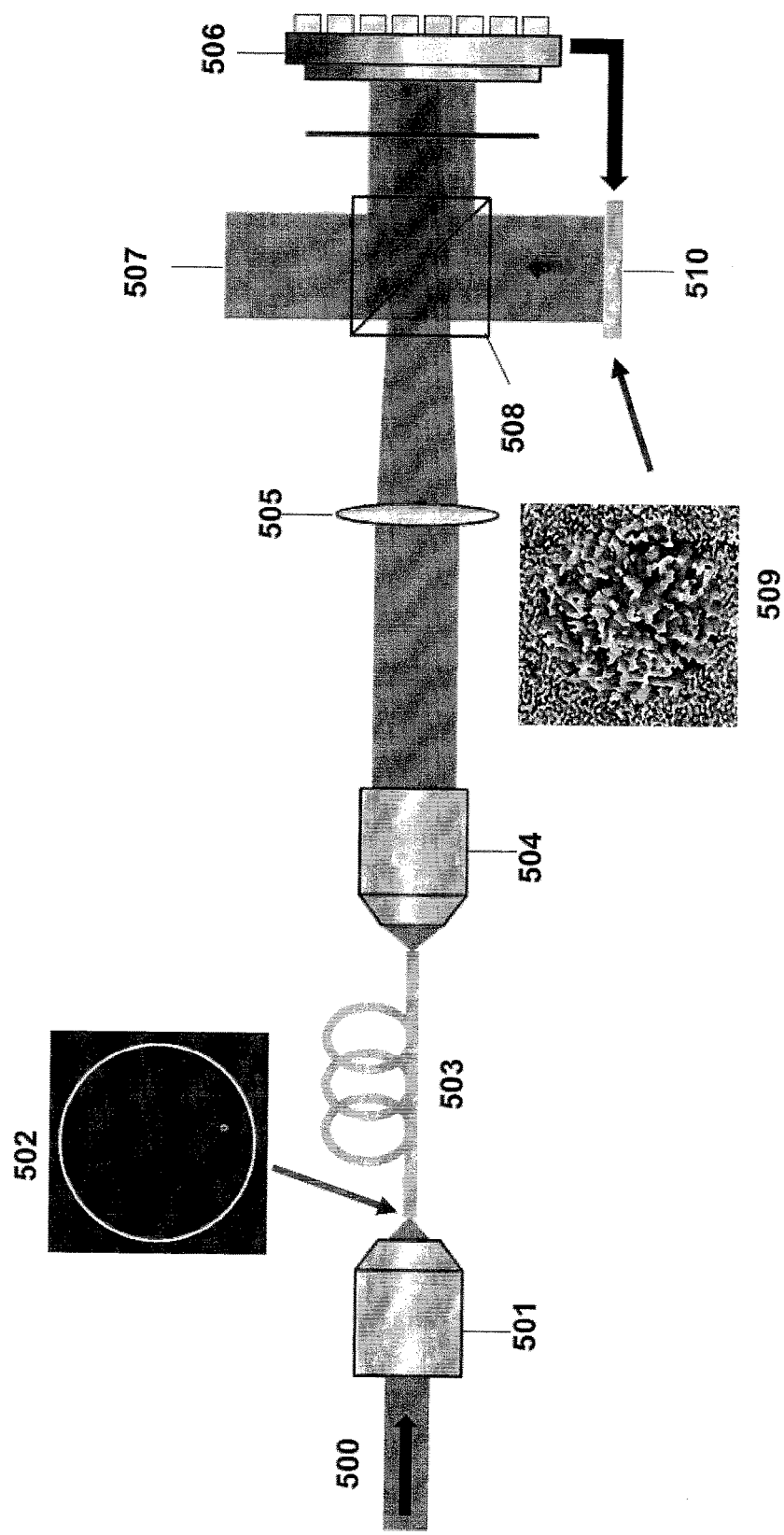
FIG. 5 shows the set-up for the implementation of digital phase conjugation in a multimode waveguide.

The experimental set-up for the implementation of digital phase conjugation through a multimode fiber is shown in FIG. 5. The calibration point source is obtained by focusing beam 500 with a high numerical aperture microscope objective 501. The calibration point source, displayed as a dot on the lower right in image 502, is injected in the multimode fiber 503 at its distal end. The facet at the other end of the fiber is imaged via objective 504 and lens 505 on image sensor 506. A reference beam 507 is combined with the output beam of the fiber by beams-splitter 508. An off-axis interferogram of the two beams, also called hologram, is recorded by the image sensor 506. The recorded hologram is then treated numerically and the phase of the optical field on the output facet of the fiber is retrieved. The calculated phase pattern 509 is then displayed onto spatial light modulator 510. Reference beam 507, incident on 510, generates a diffracted beam exactly counterpropagating the output beam (so-called phase conjugated beam). Finally, the conjugate optical field that is generated in this way is reflected back into the imaging line by beam-splitter 508 and projected onto the multimode fiber facet. The conjugated field propagates backward through the multimode optical fiber 503 and is focused at the distal end of the fiber, recreating point source 502.

Figure 6:
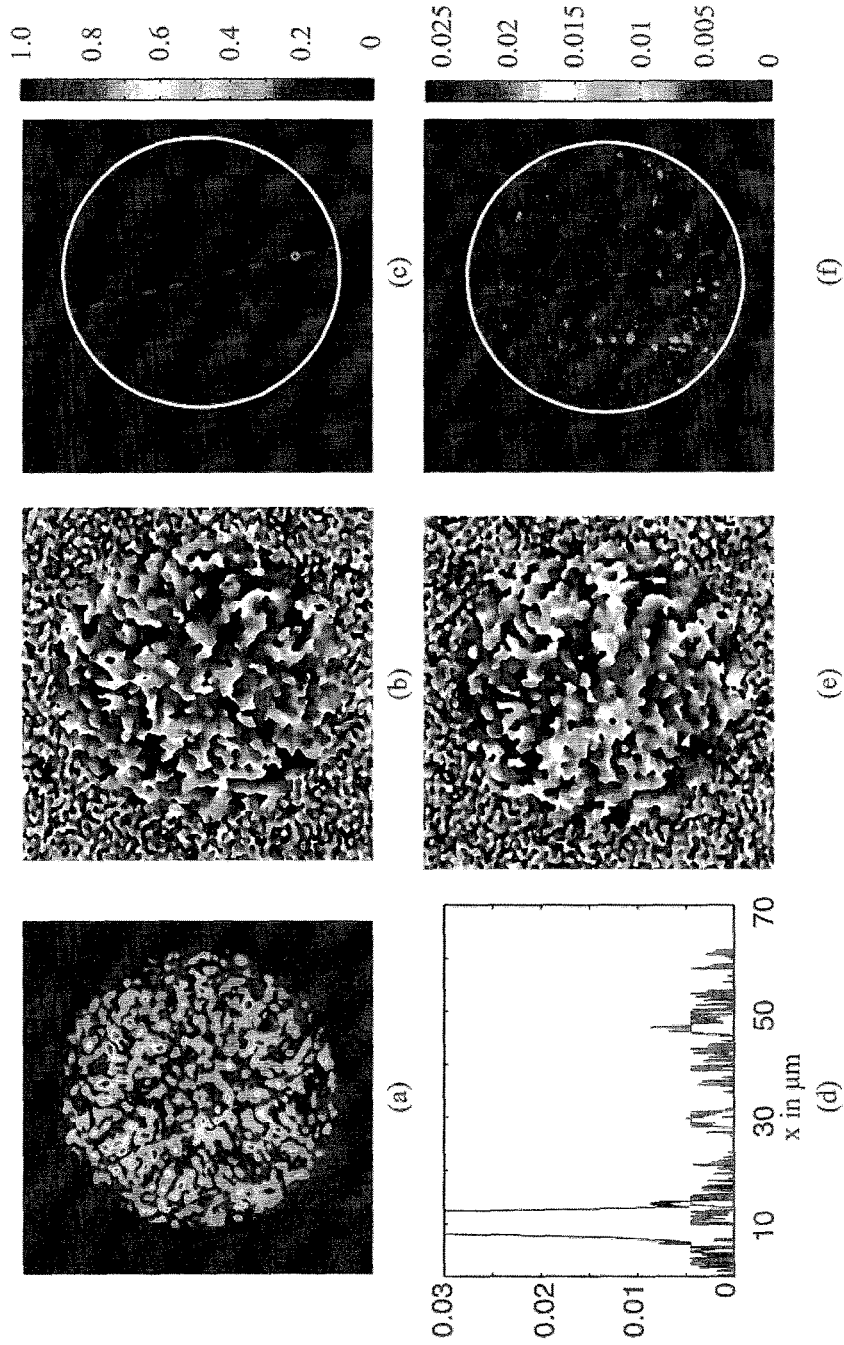
FIG. 6 shows images of a focus spot after digital phase conjugation through a multimode waveguide.

FIG. 6(a) to (f) shows experimental images illustrating focusing through a multimode fiber using digital phase conjugation. FIG. 6(a) is a speckle pattern at the output of the fiber as a result of a point source excitation launched at the multimode fiber input. FIG. 6(b) is the calculated phase from the interferogram (not shown). FIG. 6(c) is the phase conjugated focus point at the input of the fiber. The focus is created at exactly the same position as the excitation. FIG. 3(e), (f) show the result when a random phase pattern is assigned to the SLM and its corresponding image at the output of the fiber. Clearly no focusing effect can be observed. FIG. 3(d) shows the profile of the phase-conjugated spot along the red dashed line drawn in FIG. 3(c) and FIG. 3(f). Without the phase conjugation the field appears as random speckles. The white circle in FIG. 3(c) and FIG. 3(f) defines the multimode fiber core.

Figure 7:
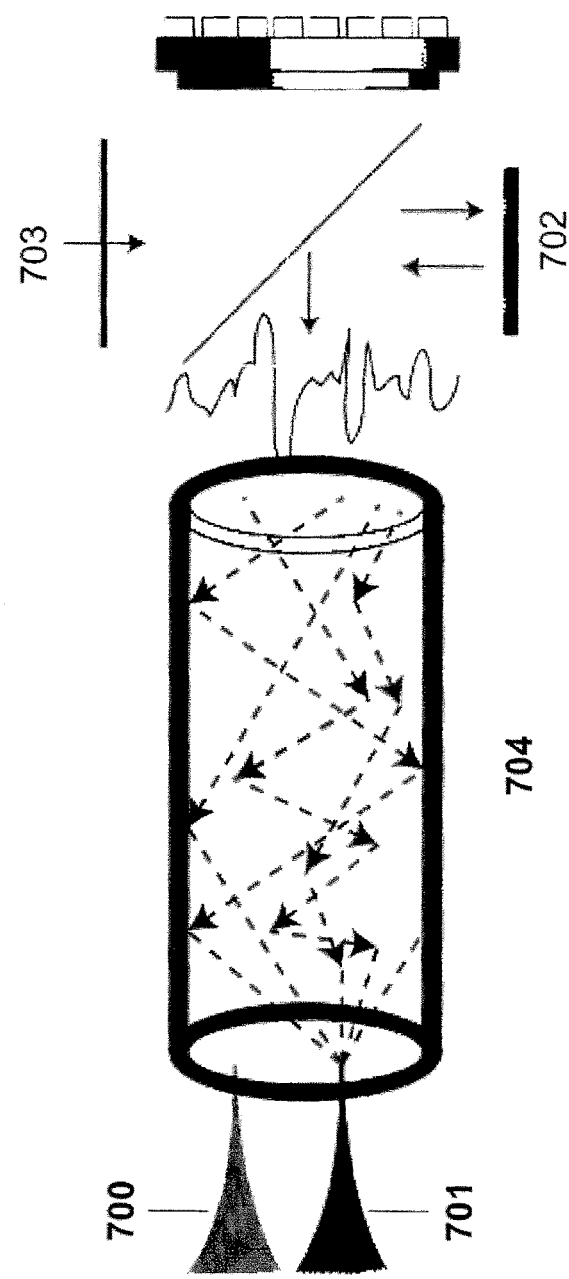
FIG. 7 shows the principle of scanning a focal point through a multimode waveguide by digital means.

FIG. 7 illustrates digital scanning of a focal spot at the distal end of the multimode fiber 704. The phase patterns corresponding to each point source 700 and 701 at the distal end of the fiber are digitally stored and sequentially displayed onto the spatial light modulator 702 which is readout by reference beam 703 to produce the required phase conjugated beam. This system generates optical scanning of a focus spot at the distal end of the multimode fiber 704 without any mechanical actuation.

Figure 8:
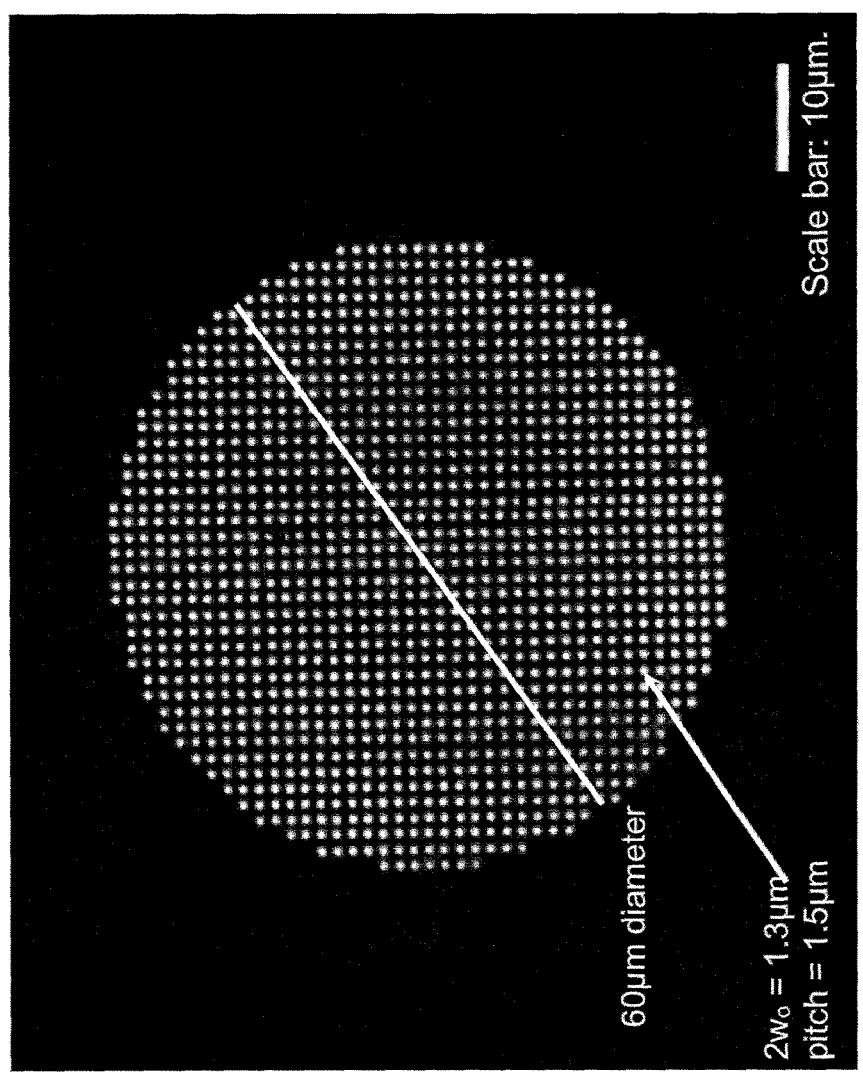
FIG. 8 shows an experimentally generated array of focal points through a multimode fiber by digital phase conjugation.

FIG. 8 shows overlaid images of ~1000 focused spots generated 200 μm away from the multimode fiber tip. The scanning region has a diameter of 60 μm, the spots have a waist of 1.4 µm and the pitch of the regular grid is 1.5 µm. Each spot is generated alone at the field of view and has a contrast >2000 with respect to the background. The scanning speed of the system is limited by the SLM refresh rate of 60 Hz. Scale bar equal to 10 µm. With digital micromirror-based SLM, the refresh speed can reach up to 23 kHz (Texas Instrument DLP), hence decreasing the scan time from 16 seconds to 43 milliseconds for 33×33 pixels image or from 2 minutes 40 seconds to 0.43 seconds for 100×100 pixels image.

Figure 9:
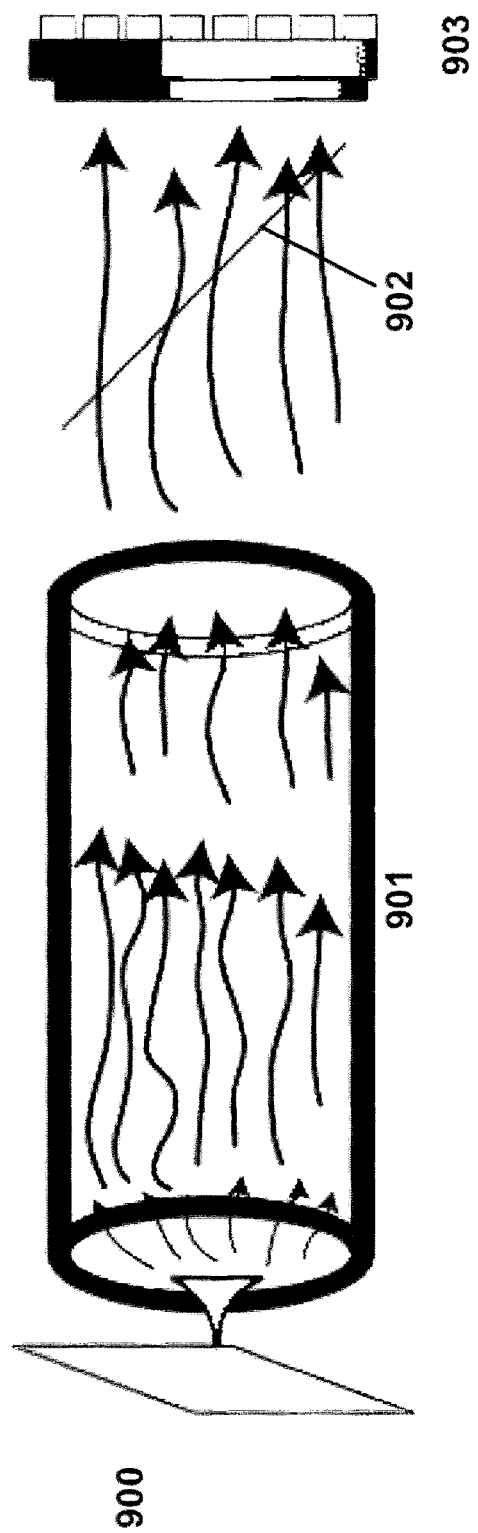
FIG. 9 shows the principle of scanning fluorescence imaging by scanning a focal spot at the tip of a multimode waveguide.

FIG. 9 describes the collection capabilities of a multimode fiber. When a fluorescent sample 900 is excited by a focus spot (excitation spot) generated via the multimode fiber by the endoscopic system described above, the fluorescence signal 901 is collected back through the same fiber and collected on the detector 903. A dichroic filter 902 blocks the linearly scattered light by the said excitation spot and transmits the red-shifted fluorescent light. An image is formed by sequentially scanning the excitation spot in the field of view of the multimode fiber and detecting the fluorescent light.

Figure 10:
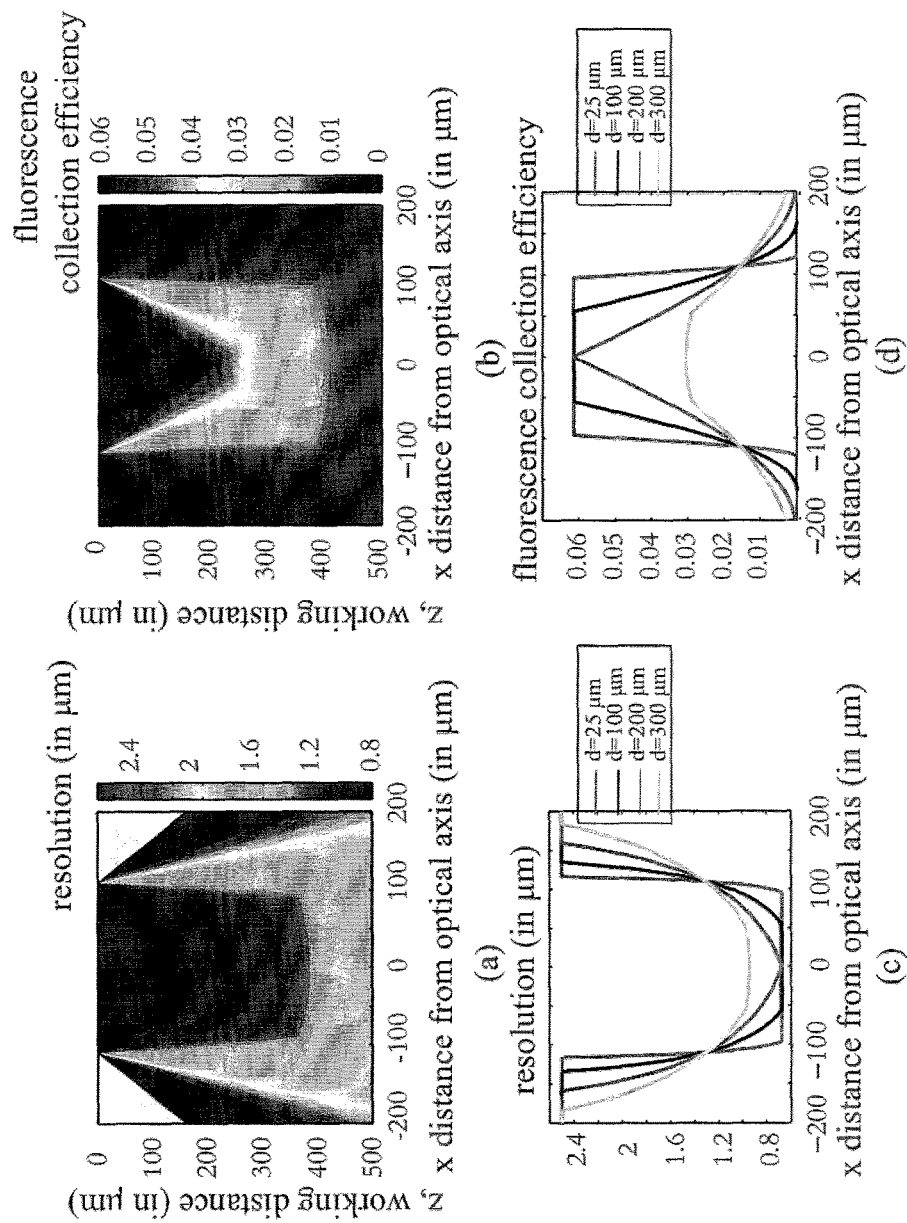
FIG. 10 shows the optical resolution of the spot size as a function of axial and lateral dimensions from the tip of a multimode waveguide.

FIG. 10 shows the resolution and fluorescence collection efficiency of the fiber endoscope as a function of working distance z and the distance from the optical axis of the system x as calculated using a geometrical optics analysis. The calculations are done, by way of example but not limited to, using a 220 µm fiber core diameter, 0.53 NA and visible light. As shown in FIGS. 10(a) and (c), the resolving power of the imaging system becomes worse as the imaging plane is set away from the fiber tip while at the same time, the useful field of view increases. The figures indicate a clear trade off between resolution and field of view. FIG. 10(b), (d) present the fluorescence collection efficiency of the imaging system as a function of position. The efficiency is worse as the fluorophore is placed away from the fiber facet and towards the edges of the field of view. The simulations can help us predict the behavior of the system and correct any differences in the fluorescent levels of the final image.

Figure 11:
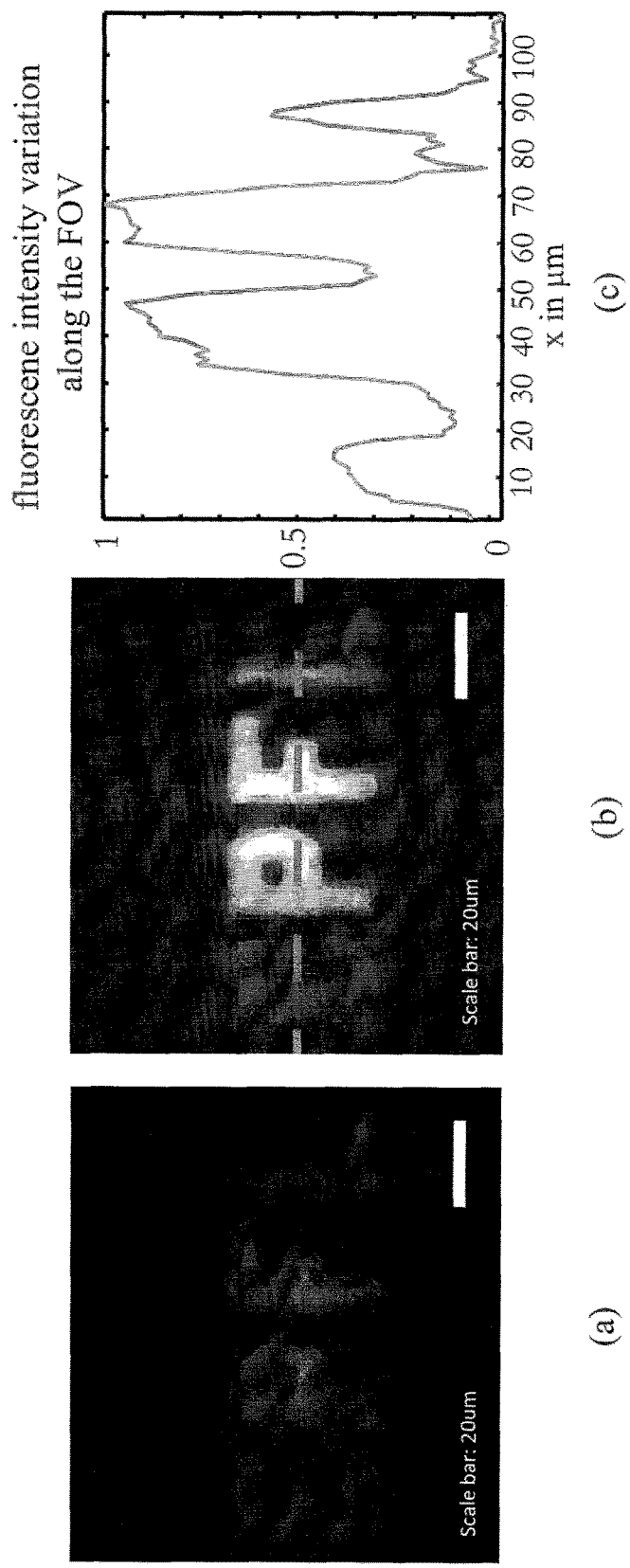
FIG. 11 shows an experimental scanning fluorescence image obtained by digital phase conjugation through a multimode fiber.

FIG. 11 shows the large field of view accessible with the multimode fiber scanning fluorescence imaging apparatus described above. The wide-field fluorescence image of a fluorescent pattern "EPFL" on a glass slide prepared with photolithography is shown in FIG. 11(a). FIG. 11(b) is the scanning fluorescent image obtained with the fiber endoscope described above at a working distance of 200 µm. The difference in the fluorescence level between the center and the edges is attributed to the different collections efficiencies away from the optical axis of the fiber and the quasi linear dependence observed coincides with the predicted behavior for the specific working distance. The endoscope is capable of providing high information capacity, large field of view images. Scale bar equal to 20 mm.

Figure 12:
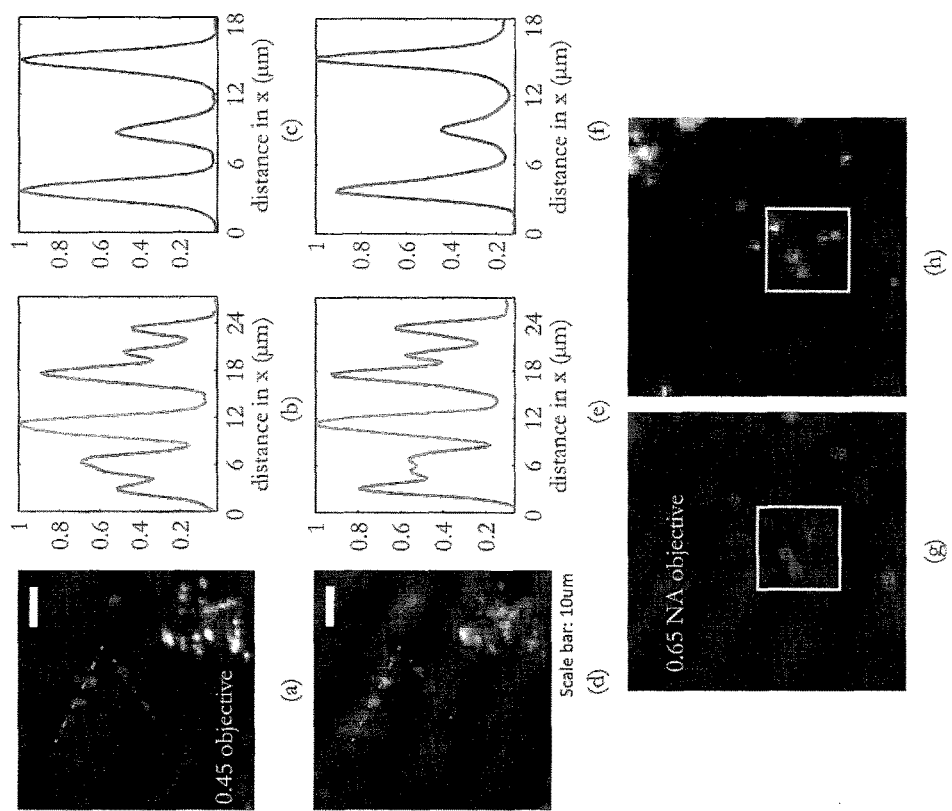
FIG. 12 shows another example of an experimental scanning fluorescence image of fluorescent beads obtained by digital phase conjugation through a multimode fiber and demonstrating sub-micrometer resolution.

FIG. 12 demonstrates the high-resolution capability of the multimode fiber endoscope by providing a comparison with a conventional wide-field optical system of the same numerical aperture and estimated resolution. FIG. 12(a) shows a widefield image obtained with a 0.5 NA microscope objective and FIG. 12(d) shows the same sample obtained with the multimode fiber. The information conveyed by the lensless multimode fiber endoscope is directly comparable to that given by the 0.5 NA microscope objective. The comparison of the cross sectional plots (b),(e) and (c),(f) verifies the conclusion. FIG. 12(g) and (h) are used to estimate the resolution of the system. In FIG. 12(g), the bead sample is imaged with a 0.65 NA objective to obtain a more detailed view. The multimode scanning fiber system (with a pixel pitch of 0.5 um) gives an image in which the two beads, almost fused into each other, can be still be resolved. Therefore, the resolution limit of the system is in the submicron range. Scale bars in all images are 10 mm.

Figure 13:
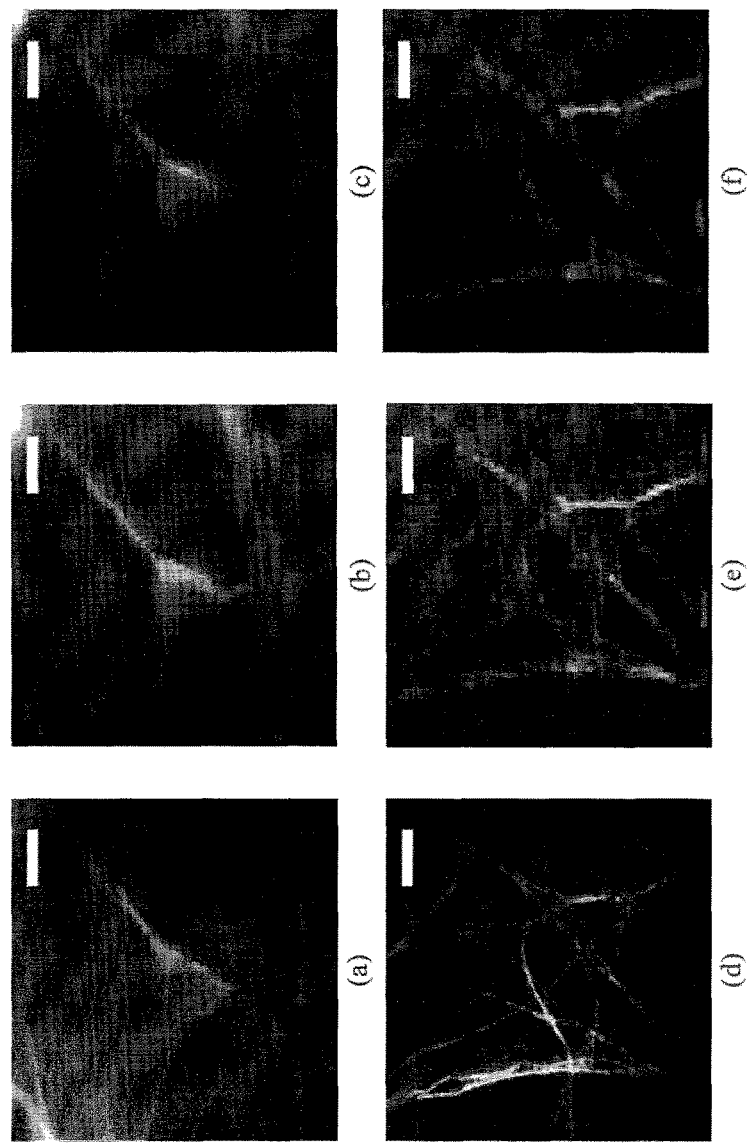
FIG. 13 shows an experimental scanning fluorescence image of a neuron labeled with fluorophores obtained by digital phase conjugation through a multimode fiber.

FIG. 13 shows images of the cellular and subcellular structure of neurons obtained with the multimode fiber endoscope described above. Images of fluorescently stained neuronal cells acquired with the multimode fiber endoscope are compared with conventional wide-field images acquired with a microscope objective. The first column in FIG. 13(a) shows a wide-field fluorescent image of a single neuron soma and FIG. 13(d) shows details of dendrites. The middle row in FIG. 13(b) and (e) shows the raw fluorescent image acquired with the fiber endoscope and FIG. 13(c) and (f) show resampled and filtered images 13(b) and (e), so that the pixelation induced by the scanning acquisition is smoothed. Highly detailed images of the neuronal soma and the dendritic network can be resolved by the multimode fiber imaging system. The high quality of the images can make this endoscope useful for diagnostic purposes based on cellular phenotype. The working distance is 200 mm to compensate for the coverslip that separates the cells from the fiber facet. Field of view is 60 mm by 60 mm and scale bars in all images are 10 mm.

Figure 14:
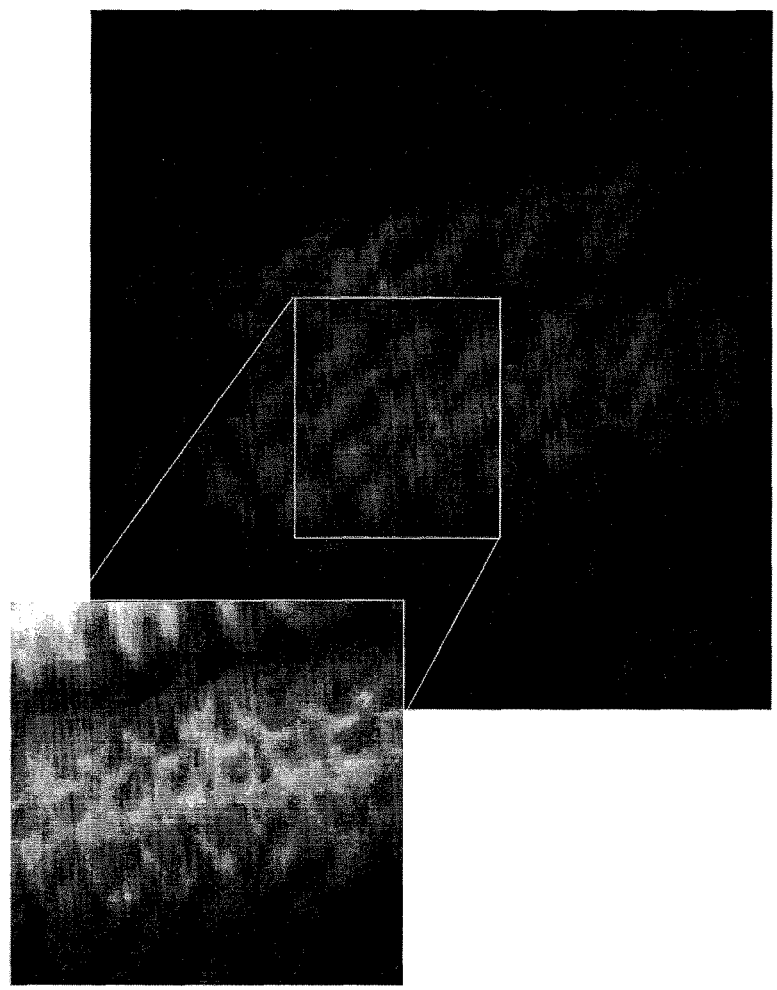
FIG. 14 shows an experimental scanning fluorescence image of the cochlea's hair cells labeled with fluorophores obtained by digital phase conjugation through a multimode fiber.

FIG. 14 shows images of a fluorescently stained pig's cochlear hair cell obtained through the round window with the multimode fiber endoscope described above. The three rows of hair cells can be clearly seen. This demonstrates the capability of the multimode endoscope to image features of the cochlea. The small size of multimode endoscope makes it suitable to image the cochlear in-vivo in humans for diagnostic purposes.

Figure 15:
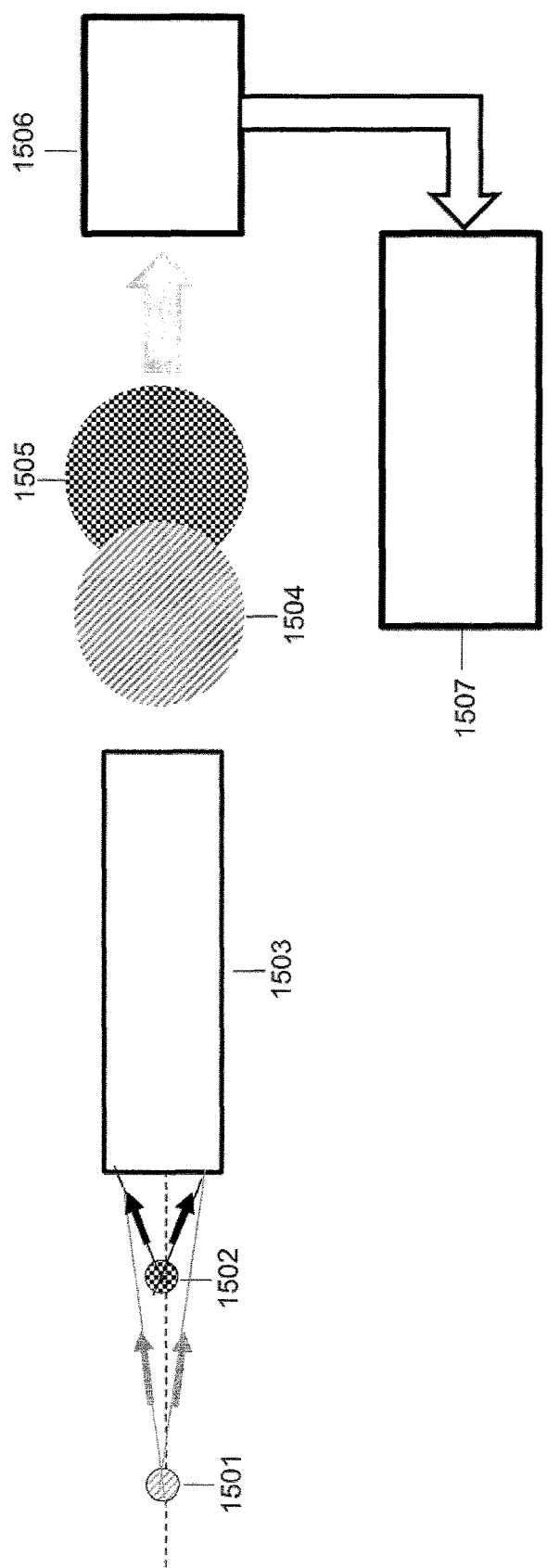
FIG. 15 shows focusing in axial direction to generate image sectioning.

FIG. 15 shows a concept to obtain axial depth sectioning in an image. A two-dimensional sensor 1506 captures the speckle patterns 1504 and 1505. Patterns 1504 and 1506 correspond to linearly scattered light from point sources 1501 and 1502 respectively after propagation in the multimode waveguide element 1503. A database 1507 of speckle patterns is recorded corresponding to an ensemble of scattered point sources distributed in the field of view of the multimode fiber. A 3-dimensional sample is illuminated through the output of the multimode fiber 1503 which can be for example, but not limited to, a plane wave. The resulting scattered speckle image is captured by the 2-D sensor 1506. This image is then correlated with the speckle patterns of the database. A 3-dimensional image is then constructed by assigning the value of the correlation for each spatial location of the known reference patterns.

Figure 16:
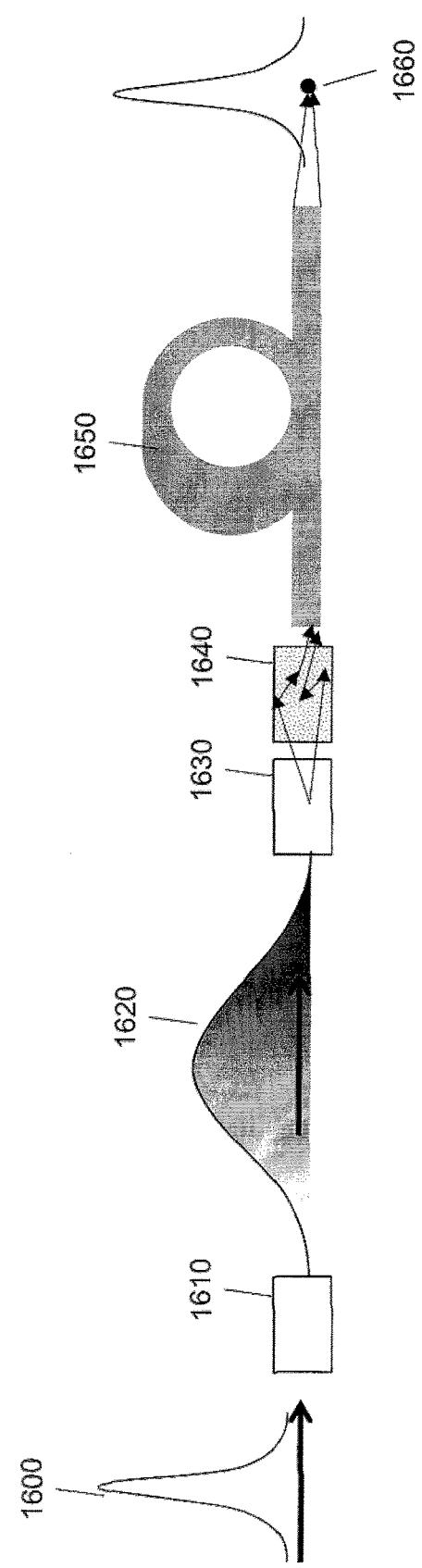
FIG. 16 shows a schematic for conditioning the spectral-time pulse shape of an ultra-fast pulse to focus in time and space at the distal tip of a multimode waveguide.

FIG. 16 shows a concept to achieve both spatial focusing and temporal focusing at the output of a multimode fiber. First, a transform limited ultra-fast pulse 1600 is temporally stretched with a suitable pulse stretcher 1610 which can be static or dynamic (SLM) to generate pulse 1620 which is then spatially modulated by a spatial light modulator 1630. The modulated wavefront is then incident on a diffuse medium 1640. The scattered light is focused onto a multimode waveguide element 1635, such as a fiber, but not limited to. At the output of the multimode waveguide element 1650, the temporal and spatial properties are entangled and by a suitable input wavefront distribution, a temporally and spatially focused spot 1660 is generated.

Figure 17:
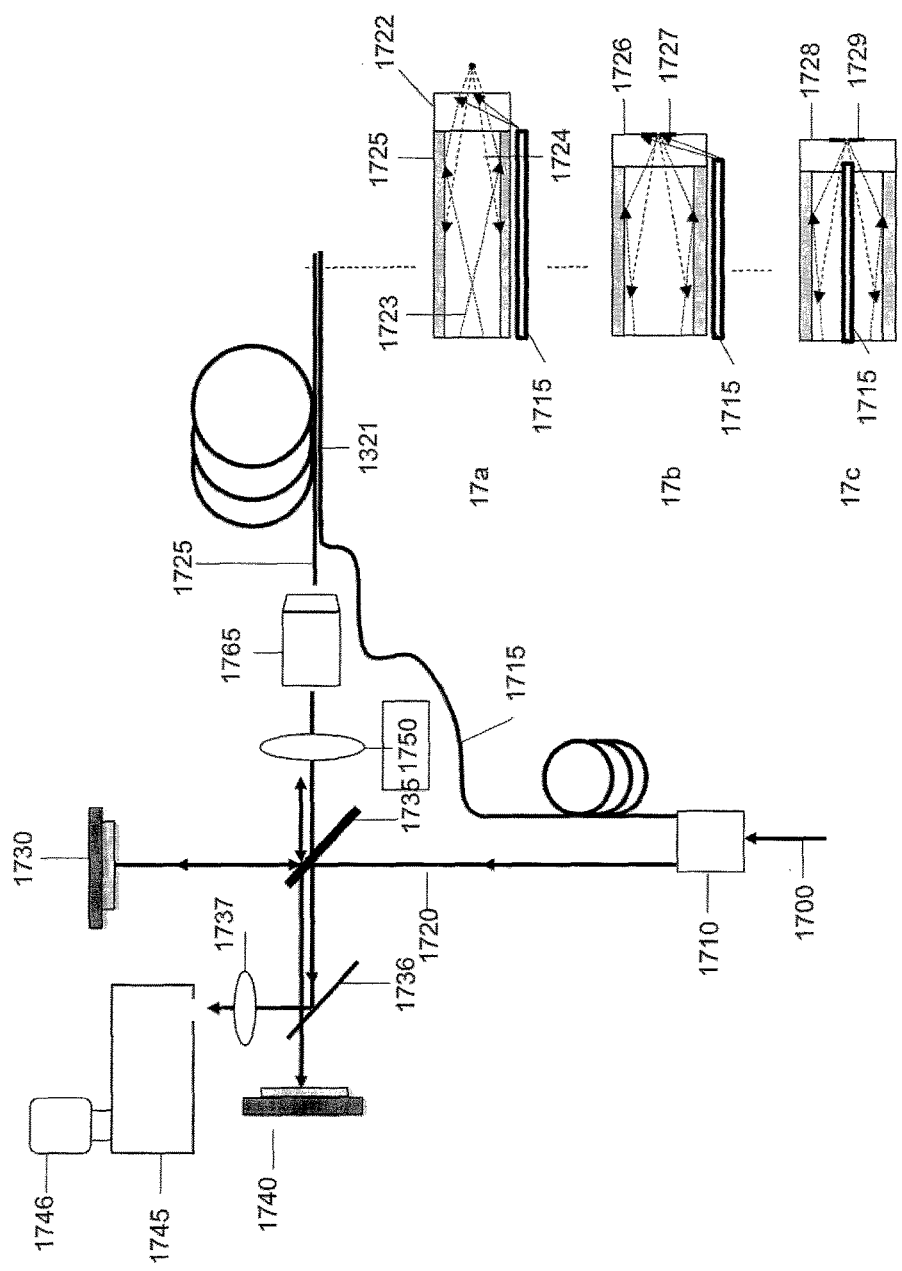
FIG. 17 shows a set-up for a Raman fiber probe system.

FIG. 17 shows a system using a multimode fiber-based Raman probe. The system consists of a Raman laser source 1700 incident on a beam splitter 1710. The beamsplitter 1710 can be a free-space beam-splitter or a fiber-based beam-splitter. The Raman laser light is split into a beacon single mode fiber reference 1715 and the beam 1720 is used for Raman excitation. The beacon fiber 1715 is either located on the side of the multimode fiber 1725 (FIG. 17(a), (b)) or inside the multimode fiber 1725, such as for example a double clad fiber (FIG. 17(c)). The role of the beacon fiber is to generate a reference beam at the distal end of the multimode fiber 1725. FIG. 17(a) shows optical element 1722 reflecting the reference beam 1715 into the multimode fiber 1725. Optical element 1722 can be a holographic element producing a virtual point source or a reflective surface producing the same. FIG. 17(b) shows optical element 1726 on which facet a reflective point source is deposited to reflect the beacon beam 1715 into the multimode fiber 1725. FIG. 17(c) shows optical element 1728 that reflects the beacon beam into multimode fiber 1725. Element 1728 can be either a holographic element, a reflective curved surface or a scattered point source deposited on the facet of element 1728. In either of the cases described by FIG. 17(a)-(c), the reference beacon 1715 propagates from the distal end of the multimode fiber 1725 to it proximal end. A microscope objective 1765 and lens 1750 images the output facet of the multimode fiber 1725 onto a 2-D camera 1740. The beamsplitter 1735 combines the speckled beacon beam coming out of the proximal end of the multimode fiber 1725 with the Raman excitation beam 1720 to form an off-axis interferogram. As is described in the invention above, the amplitude and phase of the said speckle beacon beam is calculated. The phase pattern is then displayed on the spatial light modulator 1730 to produce a phase-conjugated beam that propagates backward to the distal end of the multimode fiber 1725 to form a tight focus spot. The Raman signal generated a the said tight focal spot is collected by the same multimode fiber 1725. A dichroic filter 1736 directs the Raman signal towards a spectrometer 1745, which generates a Raman spectrum on the camera 1746. Notch filters or edge filters for excitation light rejection and are placed in the path of the Raman beam after the dichroic filter 1736 and before the spectrometer 1745. A 2-dimensional Raman image can be constructed by digitally scanning the focal point as is described in the patent above. The choice for the multimode fiber 1725 should be selected from fibers that exhibit a small Raman signal. For example, a Sapphire fiber is preferred. However standard silica based fiber can also be used because the intensity in the core of a multimode fiber of 100 micrometers diameter is approximately 10,000 smaller than the intensity at the focal spot at the distal end of the multimode fiber. Hence the Raman signal from the fiber itself is negligible compared to the Raman signal from the sample located at the focus.

Figure 18:
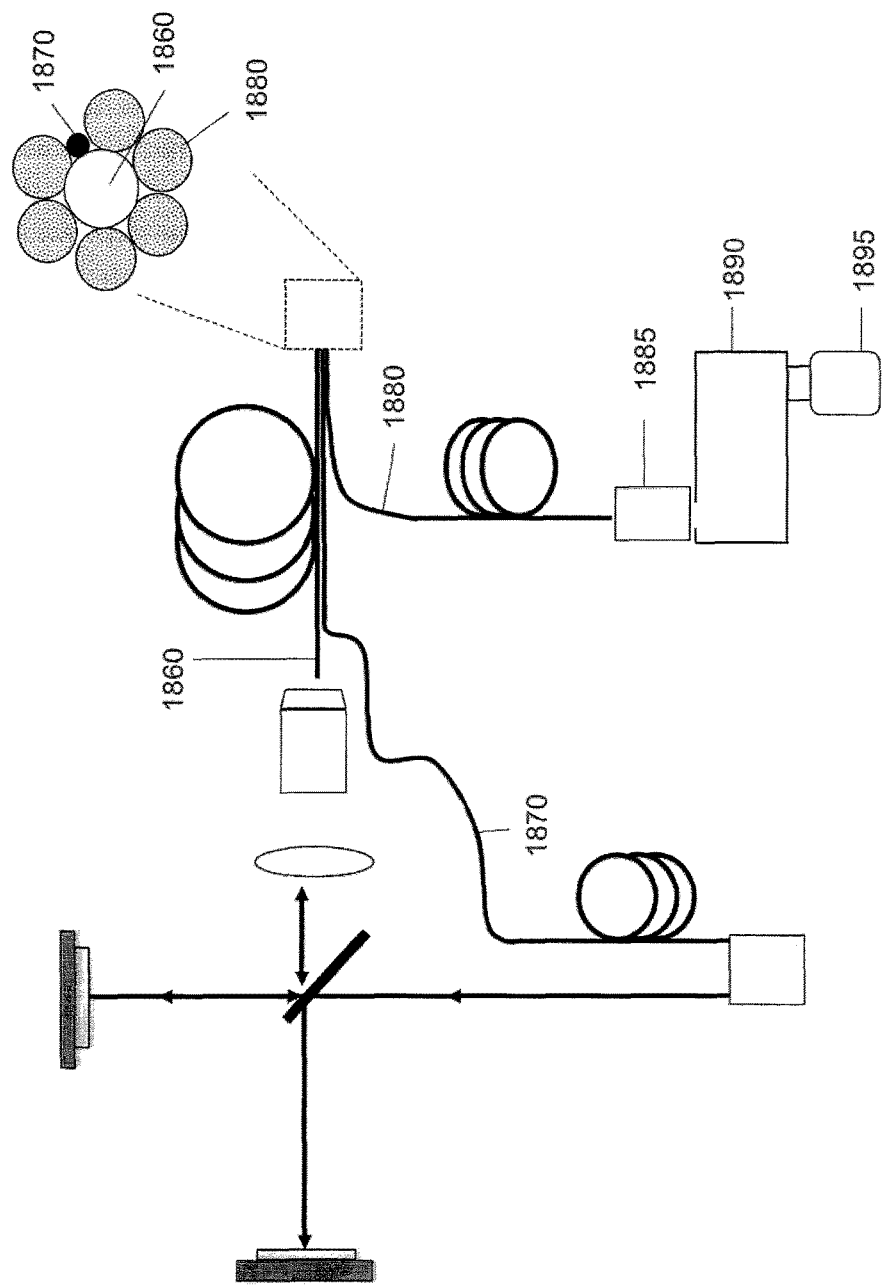
FIG. 18 shows another set-up for a Raman fiber probe system.

FIG. 18 shows another system using a multimode fiber-based Raman probe. The difference with the system in FIG. 17 is the collection multimode fibers 1880 surrounding the multimode fiber 1860 bringing the Raman excitation light. The reference beacon single mode fiber 1870 is used for providing a reference speckle interferogram identical to the system in FIG. 18. Since the collection fibers 1880 are separate from the excitation fiber 1860, the former are directly connected to a set of notch filters or edge filters 1885 to remove the excitation light prior to entering spectrometer 1890 and camera 1895.

Figure 19:
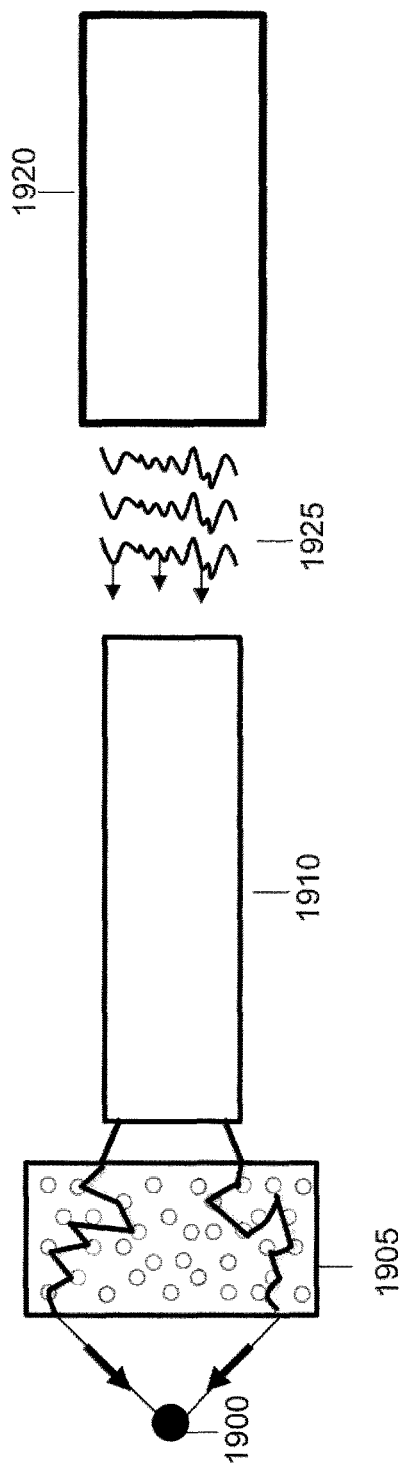
FIG. 19 shows a schematic similar to FIG. 4 but with a diffuser at the tip to increase spatial resolution and to implement space and time control on the wavefront.

FIG. 19 shows the concept for increasing the lateral resolution of the multimode fiber endoscope. The concept is also applicable to any multimode waveguide element. A scattering medium 1905 is placed at a distance to the distal end of the multimode fiber 1910. The larger the said distance is the higher is the lateral resolution. A point source 1900 is first sent through the scattering medium before being coupled in the multimode fiber 1910. A phase conjugation system 1920 described above in the present patent generates a phase-conjugated beam 1925 that reproduces the point source 1900. Because the scattering effectively increase the numerical aperture of the fiber, the spot size is smaller hence the resolution is higher.

Figure 20:
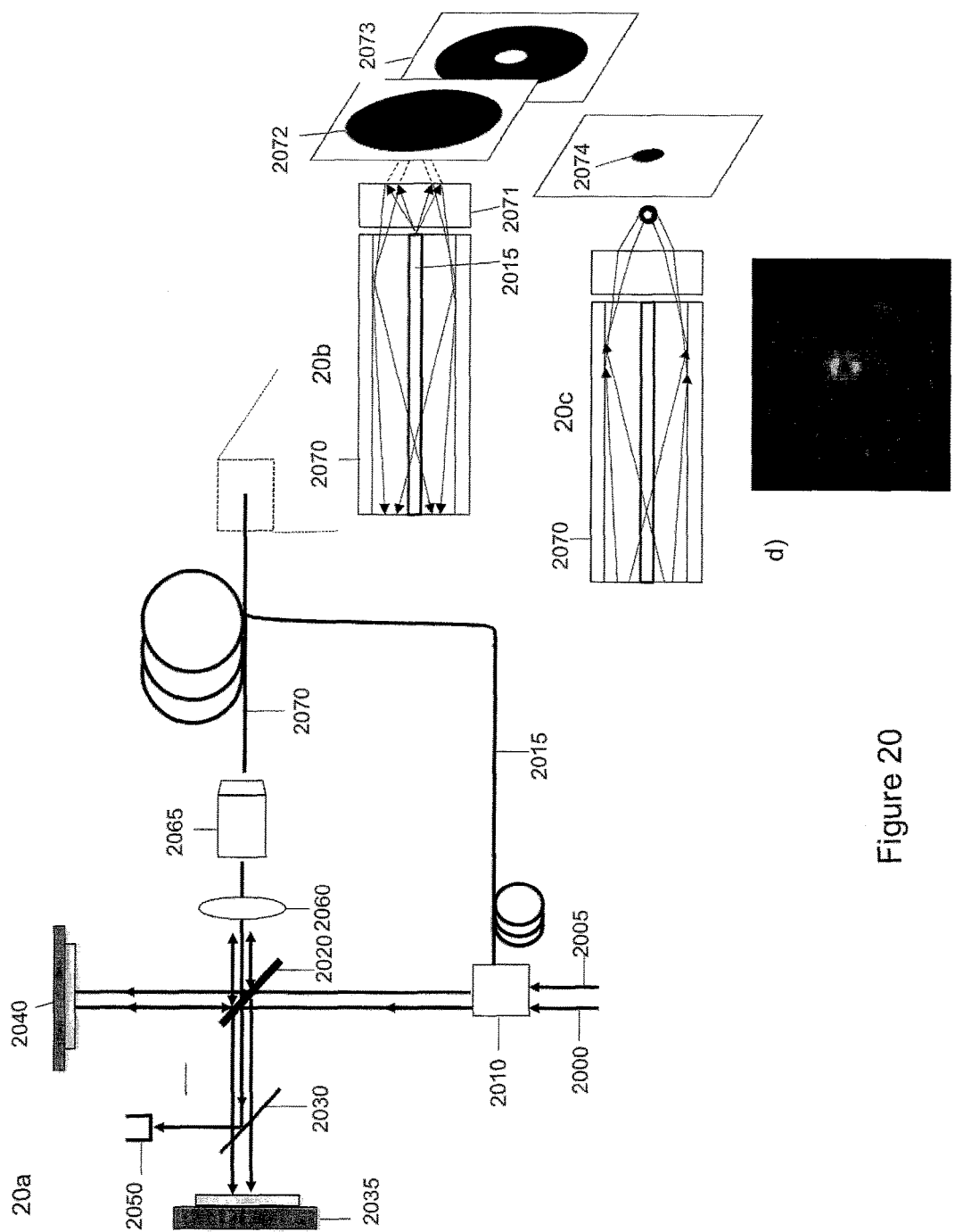
FIG. 20 shows a set-up to implement STED with a multimode waveguide.

FIG. 20(a)-(d) describes a system for providing super-resolution STED through a multimode waveguide element. A first excitation beam 2000 and a second depletion beam 2005 are both split in two by beam-splitter 2010. Beam 2000 and 2005 are independently controlled. A fraction of beam 2000 and 2005 are coupled into single mode fiber 2015 for use as a beacon reference. The other fraction of beam 2000 and 2005 are directed towards beamsplitter 2020, which splits the beams into two parts. One part is directed to digital camera 2035 and the other part is incident on spatial light modulator 2040. The single mode fiber 2015 containing beams 2000 and 2005, which are of different wavelength, is coupled to multimode fiber 2070 (via a coupler not shown). In one instance, the single mode fiber 2015 becomes the single mode fiber of a double clad multimode fiber 2070 as shown in FIG. 20(b)-(c). In FIG. 20(b), an element 2071 is attached to the distal end of the multimode fiber 2070. Element 2071 has a reflective lens or a holographic reflective film on its facet to produce a virtual point source 2072 (e.g. Gaussian) for the beam 2000 and a virtual doughnut beam 2073 for the beam 2005. The details of element 2071 are described in FIGS. 21-24. In another instance, a rigid multimode waveguide element 2070 is used. In this instance, the reference beacons 2015 may not be necessary, which simplifies the system. The focused Gaussian beam 2072 is generated by focusing a collimated Gaussian beam with a high numerical aperture microscope objective (not shown, including immersion objectives). The doughnut beam 2073 is generated by introducing a phase plate (not shown) in the path of a collimated Gaussian beam and focusing it with a high numerical aperture microscope objective (not shown). As described above in the digital phase conjugation method, phase-conjugated beams corresponding to the point source 2072 and doughnut beam 2073 are generated at the distal end of the fiber (FIG. 20(c)). The super-resolved fluorescence spot 2074 is theresult of the illumination of the excitation Gaussian spot size followed by the depletion doughnut-shaped beam. This said fluorescence is then collected by the same multimode fiber 2070 and directed to a detector 2050 by a dichroic filter 2030. An experimental image of the doughnut-shaped beam is shown in FIG. 20(d). 2060 is a magnifying lens that images, together with the microscope objective 2065, the tip of the fiber 2070 onto the 2D camera 2035.

Figure 21:
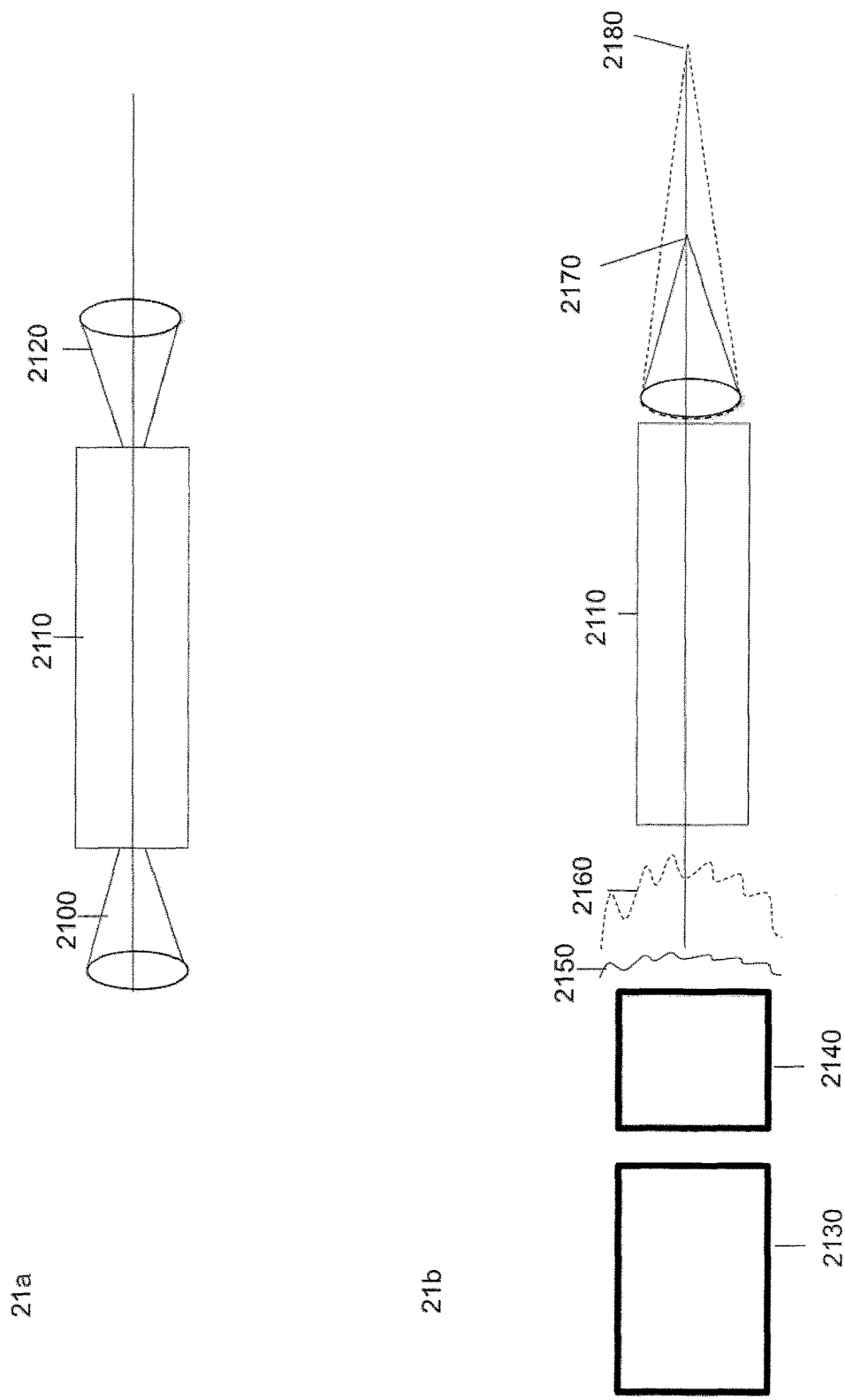
FIG. 21 shows a schematic for adapting the focus axially at the distal tip of a multimode waveguide endoscope.

FIG. 21 shows the concept for axially translating a focal spot at the distal tip of a multimode waveguide endoscope. It is well known that the azimuthal angle of a cone of light 2100 is preserved after propagation through a multimode circularly symmetric waveguide 2110 (U. Levy, A. Friesem Appl. Phys. Lett. 32, 29 (1978)). The output cone 2120 retains the same angle as the input cone 2100. This equality means that the propagation vector k in the direction of propagation z remains unchanged. In the digital phase conjugation system applied to multimode waveguides described in this patent, one can use this effect to change the axial location of the focal point generated at the distal end of a multimode waveguide. FIG. 21b shows the concept. A spatial light modulator 2130 provides a phase-conjugated beam 2150 to focus light 2170 at the distal end of multimode waveguide 2110. By providing a quadratic phase profile to the phase pattern using the same spatial light modulator 2130 or equivalently by using an additional electronically adjustable focal length lens 2140, the location of the focal spot 2170 is moved axially to focal spot location 2180.

Figure 22:
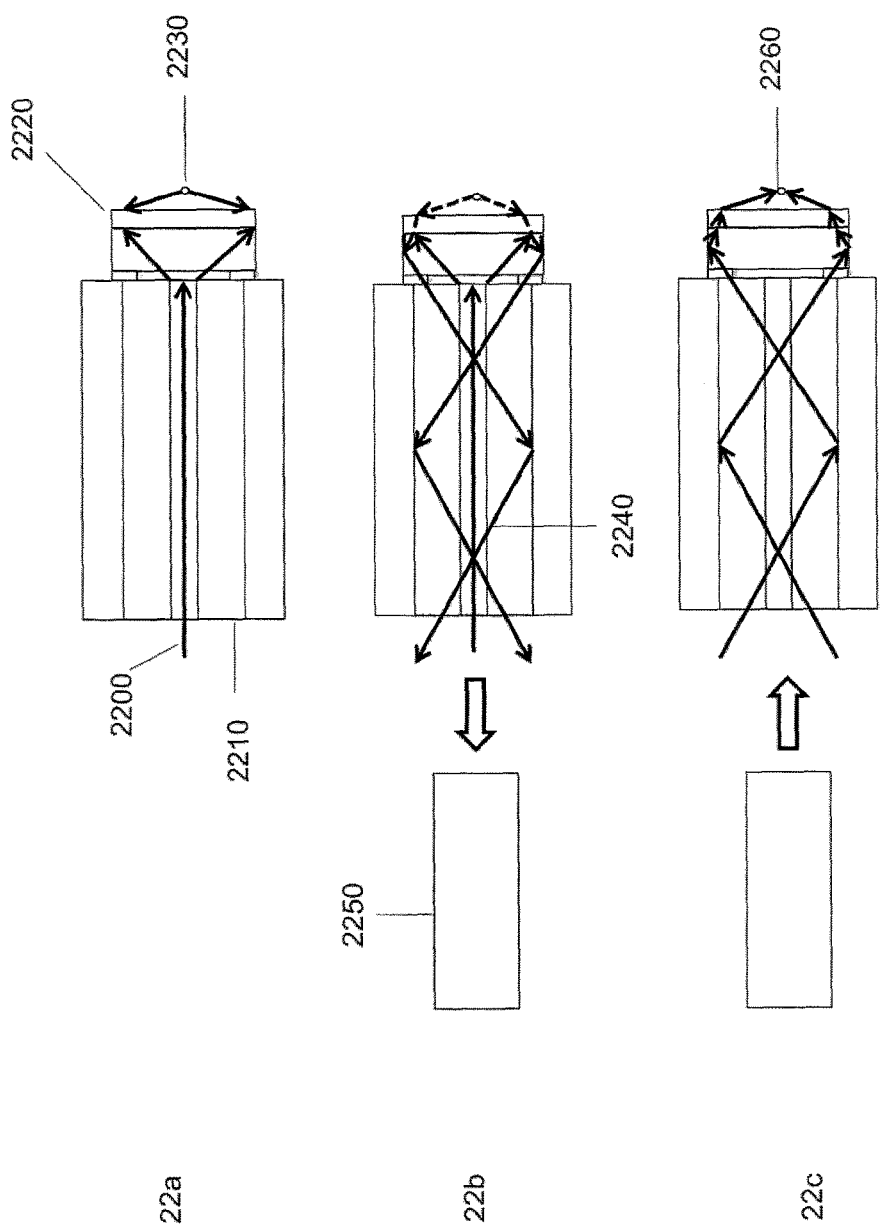
FIG. 22 shows a schematic of a reference virtual point source holographic beacon generated by propagating a beam in the single mode core of a double clad multimode waveguide.

FIG. 22 is a description of a virtual holographic beacon guided digital phase conjugation process through a double-clad fiber. First, in the holographic recording process (FIG. 22*a*), the light in the single mode fiber 2200 of the multi-mode double clad fiber 2210 interferes coherently, in reflection, with light originating from a point source 2230. The interference occurs on a holographic material 2220. The holographic material can be, but not limited to, a polymer, a photorefractive crystal, a photorefractive glass. The point source 2230 can be generated by a high a NA object or a multi-spot light pattern (not shown). The point source is located in such a way that it is coupled in the double cladding on the dual clad multimode fiber 2210. FIG. 22*b* shows the recorded holographic element 2220 illuminated by the output light from the single mode fiber 2200. Element 2220 produces diffracted light 2240, which recreates the wavefront originating from the virtual point source 2230. The diffraction efficiency of the holographic element is such that it allows an appropriate detection signal on the camera in system 2250. Diffraction efficiency values of a few percent to few ten percent are suggested. The diffracted light 2240 propagates to the proximal end of multimode fiber 2210 and whose phase and amplitude is recovered by system 2250 (described above in the patent). The phase-conjugated beam is then generated by system 2250. A real focus point 2260 is then generated (FIG. 22*c*).

Figure 23:
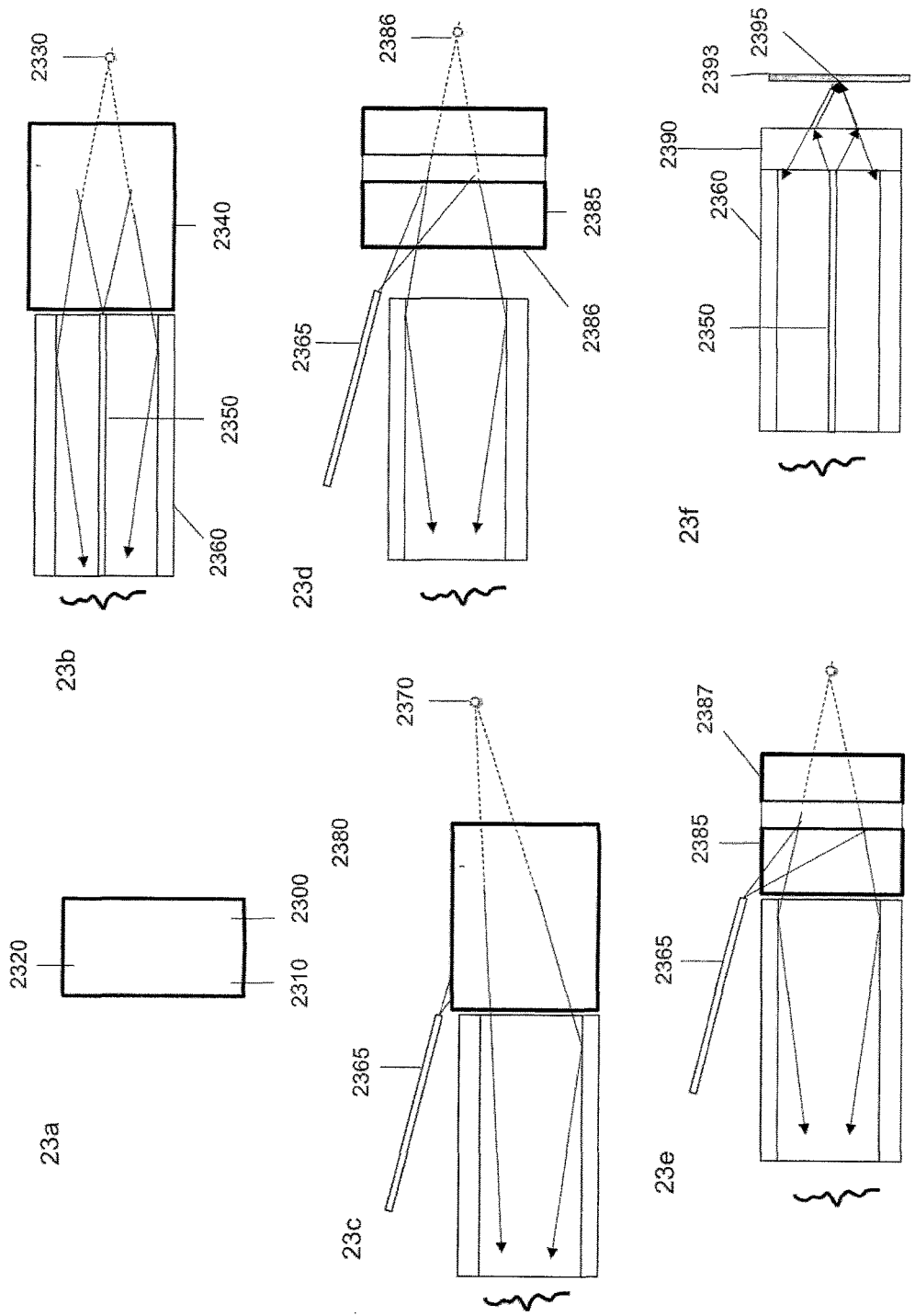
FIG. 23 shows a schematic of a reference virtual point source with a partially reflective lens or holographic grating illuminated with a reference beam from a single mode core waveguide.

FIG. 23 describes other implementations of beacon generation. In FIG. 23*a*, a partially reflective micro-lens is described. A reflective layer 2320 is on the surface of a concave (or convex) element 2300. Element 2310 protects said reflective layer 2320 and whose index of refraction should be chosen close to that the refractive index of element 2300. The reflective micro-lens may not need protective element 2310 to be functional. The reflective layer 2320 is partially reflective. It may comprise metallic coatings, dielectric coatings or any other type of reflective coating with any spectral bandpass, broad or narrow. FIG. 23*b* shows said reflective micro-lens array 2340 attached to a multimode flexible double clad fiber 2360. The output light from single mode core 2350 illuminates the micro-lens 2340 to produce reflected light that is coupled in the double cladding of multimode fiber 2360. The reflective surface of micro-lens 2340 is designed in such a way that the reflected light originates from a virtual focus 2330. FIG. 23*c* is a variation of FIG. 23*b* where the single mode fiber 2365 is not inside the multimode fiber 2360 but is located outside. Similarly to FIG. 23*b*, the output light from the single mode fiber 2365 generates a virtual focus 2370 by reflection off the partially reflective layer of the micro-lens. In FIG. 23*d*, the reflective element 2385 is a holographic element (as described in FIG. 22) illuminated sideways by single mode fiber 2365 to produce a virtual point source 2386. The light from single mode fiber 2365 enters the front side 2386 of element 2385. FIG. 23*e* shows a variation of FIG. 23*d* where the illumination side is from the top facet of element 2387. FIG. 23*f* shows a lens element 2390 attached to a double clad multimode fiber 2360 so as to form an image 2395 of the output of the single mode fiber 2350 onto a reference surface 2393 (for example, but not limited to, the surface of a microscope slide). The reflected light is then coupled in the multimode fiber 2360. In all these FIG. 23*a-f*, the reference speckle pattern at the proximal end of the multimode fiber serves as a reference. One instance, the reference is used to sense the conformation of the flexible multimode fiber so as to use the appropriate set of phase pattern to the spatial light modulator as described in the patent.

Figure 24:
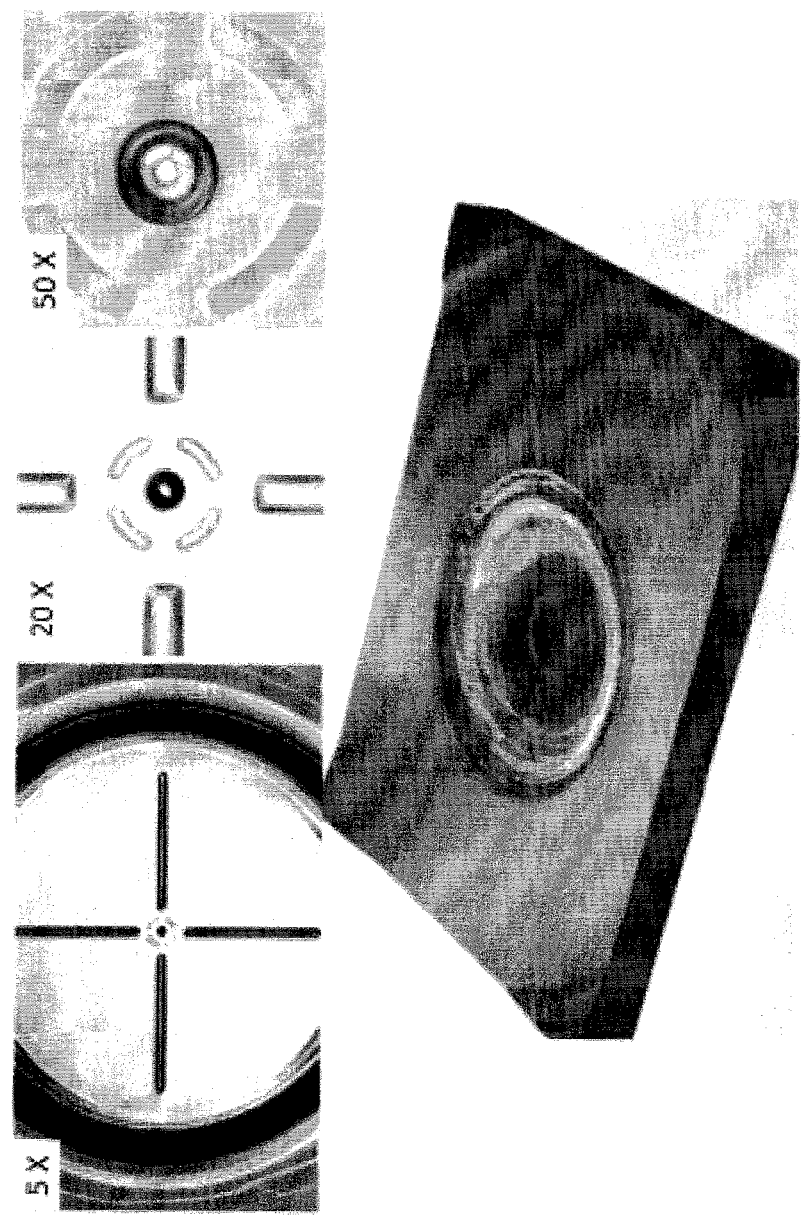
FIG. 24 shows a magnified image of a fabricated virtual beacon lens (23a).

FIG. 24 shows an image of a fabricated reflected microlens described in FIG. 23.

Figure 25:
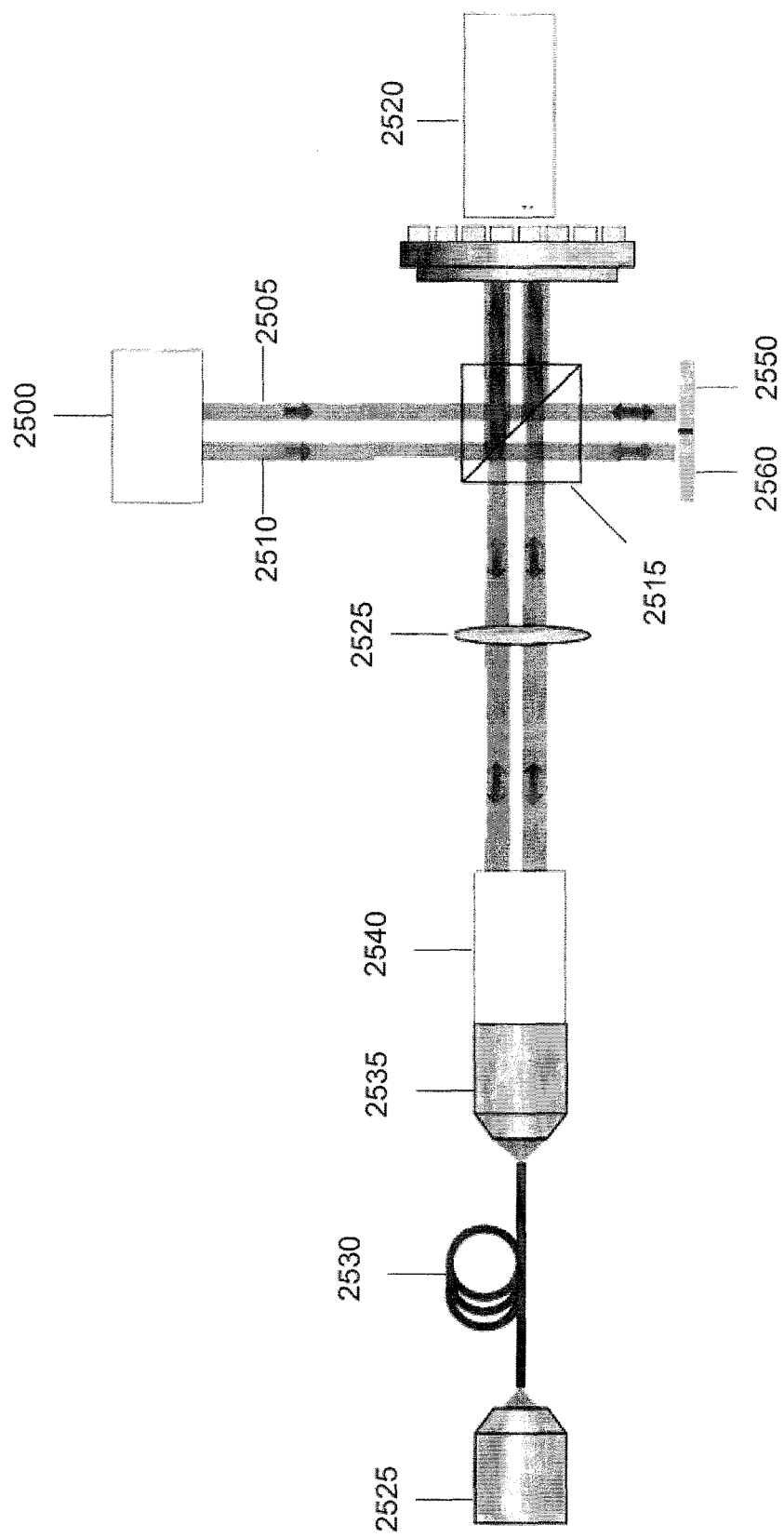
FIG. 25 shows a set-up to provide a phase-conjugated field with two orthogonal polarizations.

FIG. 25 describes a polarization preserving wavefront shaping system that improves the signal to noise ratio of the generated pattern at the output of a multimode waveguide element. This system treats both polarizations separately. A light beam produces two orthogonal polarization beams 2505 (s-polarization) and 2510 (p-polarization) using a polarizing beam-splitter 2500. A non-polarizing beam-splitter 2515 splits the beams in two directions. One direction is directed towards a 2D camera 2520 and records one interferogram for each polarization, with the light output from a multimode fiber 2530. The phase pattern corresponding to the s-polarization component is displayed on one side of the spatial light modulator 2550 and the p-polarization component is displayed on the other side 2560. The single spatial light modulator can be replaced by two spatial light modulators, one for each polarization. Alternatively a wave-plate can be added on one of the reference beams or on one side of the spatial light modulator. 2525 is a magnifying lens that images, together with the microscope objective 2535, the tip of the fiber 2530 onto the 2D camera 2520. 2540 is a polarization combiner that combines into one single beam the spatially separated s-polarized beam 2505 and p-polarized beam 2510.

Figure 26:
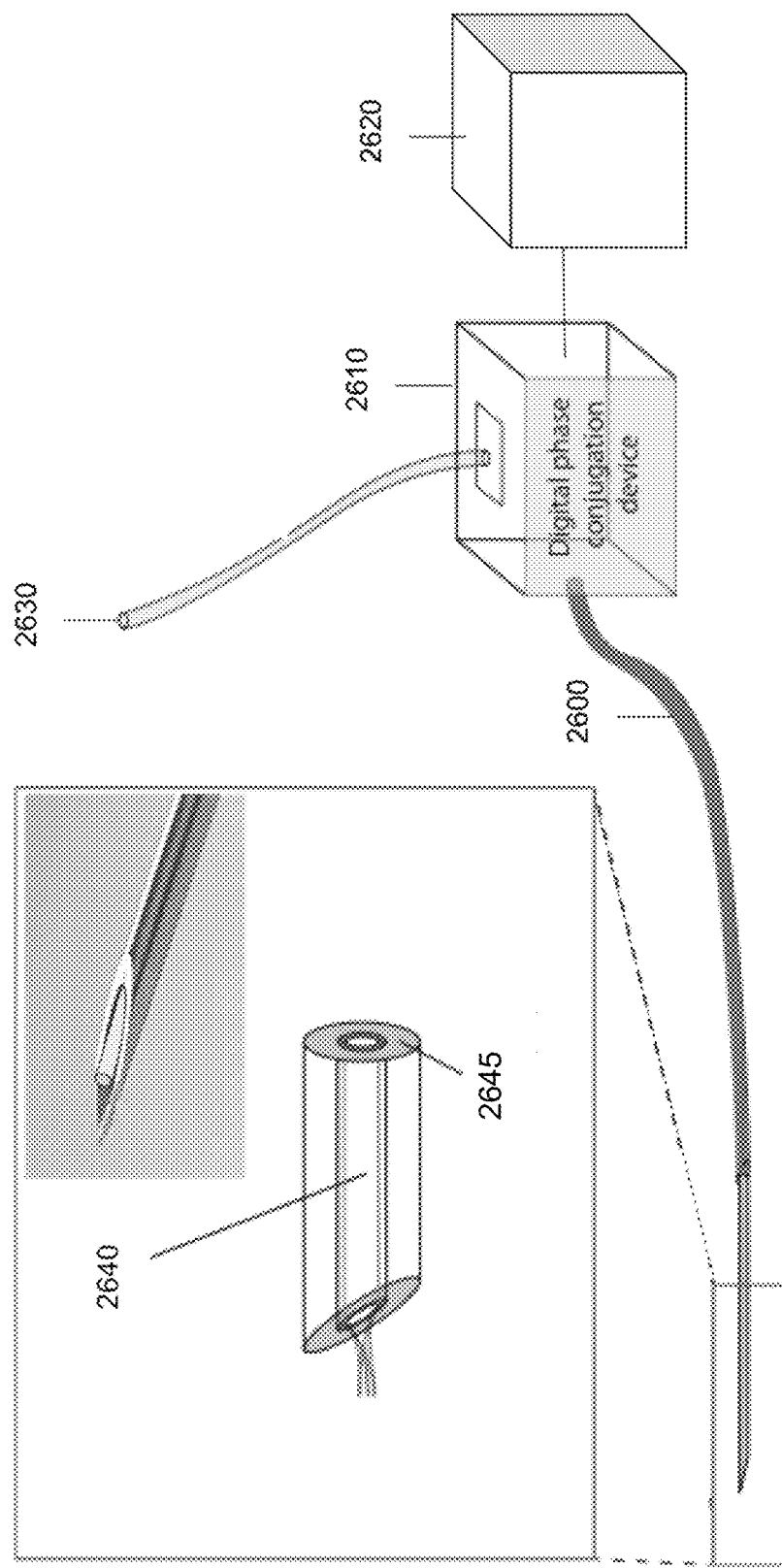
FIG. 26 shows an endoscopic system with a multimode fiber.

FIG. 26 shows a schematic of a flexible multimode fiber endoscope system with the distal end of the multimode fiber 2600 embedded into a rigid needle 2640. The rigid needle 2640 shown has an opening 2645 at its end. The rigid needle 2640 may have an opening on the side (not shown) in which case the distal end of the multimode fiber has an element (not shown) such as, but not limited to, a right angle prism to direct light to the said opening for side looking. The system of FIG. 26 is composed of a digital phase conjugation sub-system 2610 (such as described above in this patent), which is controlled by a computer 2620. The digital phase conjugation device 2610 has an optical fiber input 2630 to deliver one or more wavelength of light to the multimode fiber endoscope 2600. The multimode fiber endoscope 2600 can be embedded in a larger tube (not shown), which may contain a camera for guidance (not shown) and other illumination means. The multimode fiber endoscope 2600 is then pointed to a specific location by the user to obtain high-resolution images. In another instance, the digital imaging capability of the multimode fiber is used both as a guiding mean by using the digital focusing capability described for example in FIGS. 4,5,7,10 and 21 (low resolution, large depth) and as a high resolution instrument. The various imaging modalities such as, but not limited to, super-resolution, side viewing, total internal reflection, two photon, Raman described in this patent are all applicable to this system. The outer diameter of the endoscope is limited only by the needle and can be as small as 460 um for a 250 um cladding fiber for example.

Figure 27:
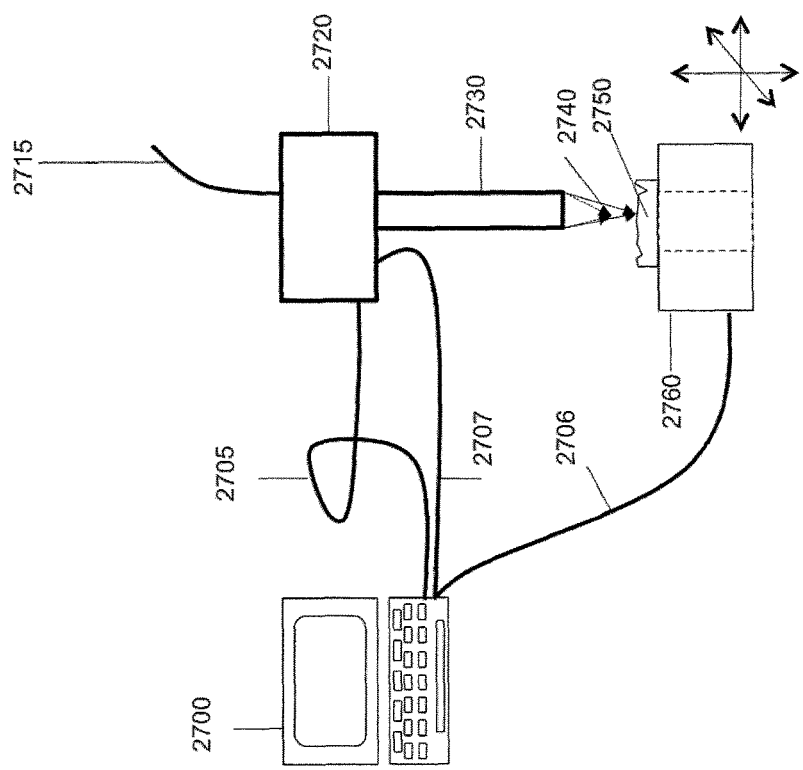
FIG. 27 shows an endoscopic system with a rigid multimode waveguide.

FIG. 27 shows a digital microscope system using a rigid multimode waveguide as the imaging component. A computer 2700 controls, via cables 2705, 2706, 2707, a digital phase conjugation sub-system (such as described above in this patent) 2720, up to three or more linear translation stages, rotation stages 2760 and one or more optical sources 2715. The imaging capability of the digital phase conjugation system 2720 described in this patent is used in conjunction with the set of stages 2760 to provide various magnification and resolution of the object under test 2750. In one instance, the field of view and magnification are determined by the distance between the distal end of the multimode rigid waveguide element 2730 and the sample under test 2750. A coarse distance value maybe determined with sensors placed appropriately on the stages 2760 and waveguide element 2730. The digital 3-dimensional focusing ability of the sub-system allows a user to view a sample with a large field of view and resolution (large distance) and then select an area 2740 to zoom-in. By appropriately moving the stages 2760 and digitally refocusing at the appropriate axial distance, a finer resolution image is generated. In contrast to standard microscopes using multiple objectives to change optical resolution and field of view, the described system uses only one optical element (2730). A thin and long (needle like) multimode waveguide element 2730 can reach areas that are not accessible with standard microscope objectives or grin lens micro-objective, which are short. A suggested size for the multimode waveguide element is, but not limited to, 0.1-0.5 mm diameter by 5-20 cm long. To avoid damage to element 2730, it maybe inserted in a solid rigid protective case. A deployable "umbrella-like" mechanism in front of the multimode fiber can be used as an inserting and protecting device. It will open up to the final form after the fiber endoscope is inserted inside the area that is to be imaged and prevent the deposition of tissue debris while the endoscopic head is inserted in the body.

The various imaging modalities such as, but not limited to, super-resolution, side viewing, total internal reflection, two photon, Raman described in this patent are all applicable to this system.

Figure 28:
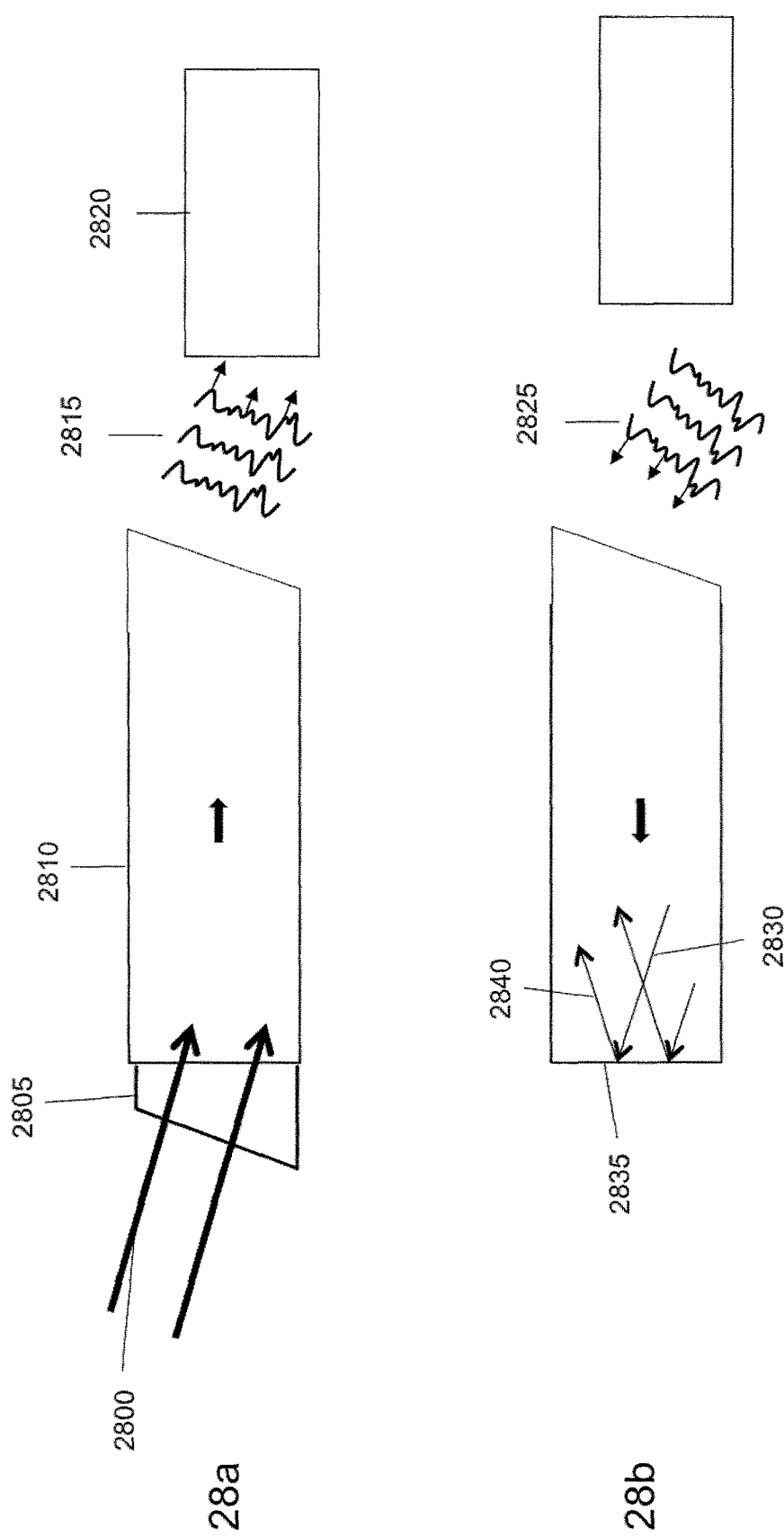
FIG. 28 shows a schematic to create a total internal reflection endoscope.

FIG. 28 is shown to form a total internal reflection microendoscope. FIG. 28a shows the calibration of the system. A plane wave 2800 is incident on a wedge prism 2805 whose index of refraction is approximately the same as the index of refraction of the core of the waveguide element 2810. The plane wave 2800 is coupled to the core of the waveguide element 2810. The output facet of 2810 is angled so as to allow the waveguided light to out-couple with low loss to form the output light field 2815. The amplitude and phase of light field 2815 is extracted by the coherent interferometric system 2820 described above. In FIG. 31b), the phase-conjugated light field 2825 corresponding to the output light field 2815 is generated by a spatial light modulator (part of 2820 but not shown). The phase-conjugated field at the distal facet end 2835 of the waveguide element 2810 is a plane 2830. The wedge prism element 2805 has been removed. The angle of the plane wave 2830 and the normal to the facet 2835 is such that it satisfies the total internal reflection condition. The reflected beam 2840 propagates back in the waveguide element 2810. The evanescent wave at the interface (not shown) has a short pentration depth (several nanometers) and thus able to probe the interface of a sample located at the fiber tip.

Figure 29:
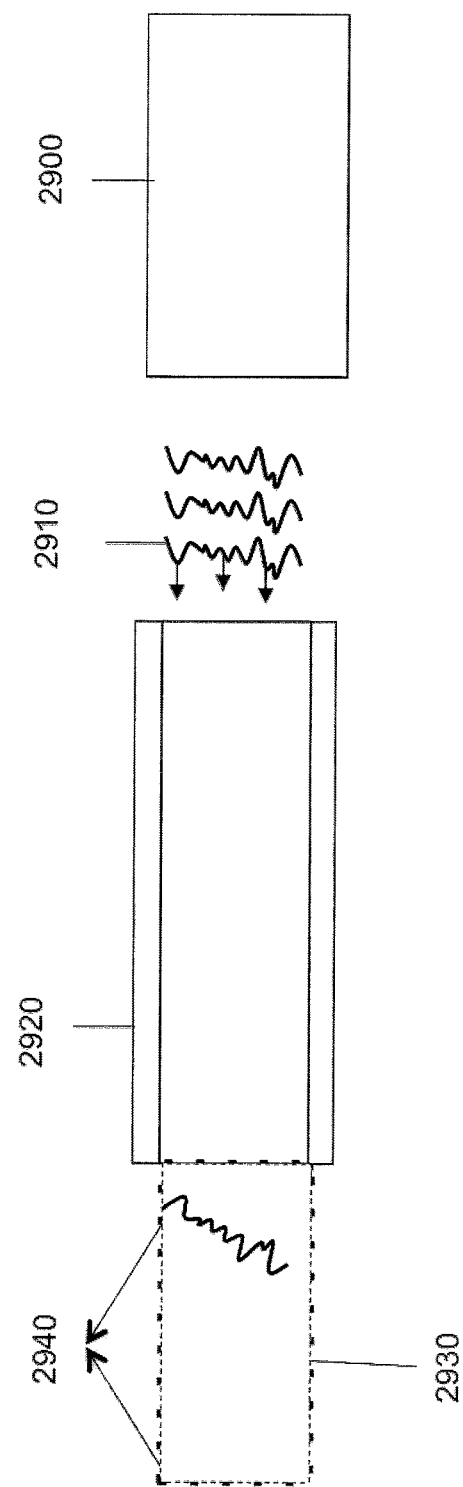
FIG. 29 shows a schematic similar to FIG. 4 but with a diffuser attached to the tip of the multimode waveguide element so as to allow light focusing and imaging on the side of the diffuser.

FIG. 29 shows a side viewing high-resolution multimode waveguide endoscope. An element 2930, which has a diffuser on its surface, is attached to the distal end of a multimode waveguide element 2920. A point source 2940 is coupled to the core of the multimode waveguide element 2920 via the diffuser. The digital phase conjugation system 2900 generates a phase-conjugated wave 2910 that recreates the point source 2940. Because the lateral side of the diffuser element 2930 is large, hence the numerical aperture in this direction is larger than in the orgthogonal direction (limited by the diameter of element 2930). Therefore the spot size has a high resolution in the direction of the length of element 2930. By mapping spots around element 2930 at least two pi steradian field of view is obtained.

Figure 30:
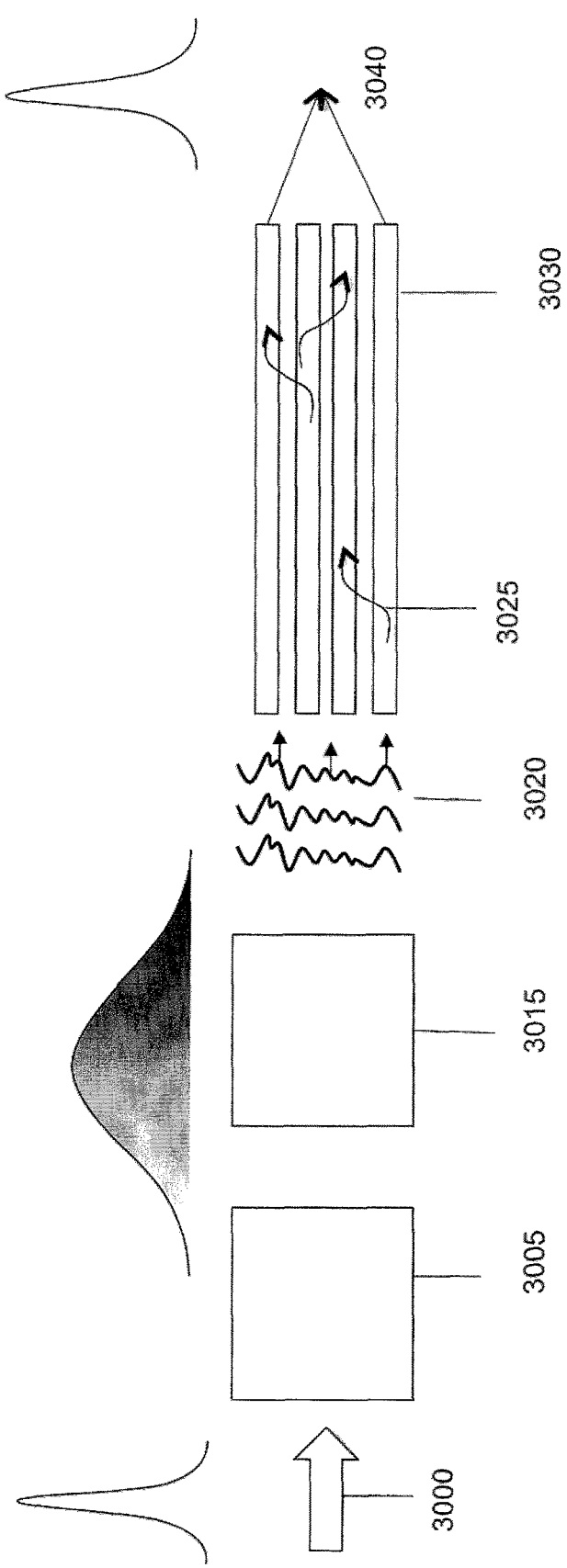
FIG. 30 shows a schematic of using a bundle of single mode waveguide element and phase conjugation system to focus in space and in time at the tip of fiber bundle element.

FIG. 30 shows a system schematic to achieve short pulse delivery and high relosution at the distal end of a coherent fiber bundle. A short pulse 3000 (tends of femtoseconds to hundreds of femtoseconds) is incident on a pulse shaper 3005 that impart an amount of dispersion on the pulse. A spatial light modulator or a digital phase conjugation subsystem 3015 provides a phase-conjugated beam 3020 as described in the patent. The waveguide element 3030 is a fiber bundle of single mode fibers or multimode with a low number of modes (<10). A typical fiber bundle can have several thousands to tens of thousand fibers. Typical distance between fibers is 3 micrometers, however the distance can be several tens of micrometeres. With 3 micrometers pitch, there is a significant cross-talk between fibers (3025) when the wavelength is large so as to obtain single mode operation. As a result, for small fiber pitch, light launched at one fiber comes out at multiple fibers on the other side. However, because the dispersion in a single mode fiber, is mainly dominated by chromatic and not modal dispersion as in multi-mode fiber, the waveform 3020 has a chromatic dispersion that is equal but with oppsite sign to the dispersion of the single mode fibers 3030. The spatial phase modulation of beam 3020 is such that each fiber of the fiber bundle 3030 at the distal end acts as a phased array antenna that tightly focuses the beam at an axial distance 3040. The pulse is recompressed in time due to the opposite sign of dispersion of the single mode fibers.

Figure 31:
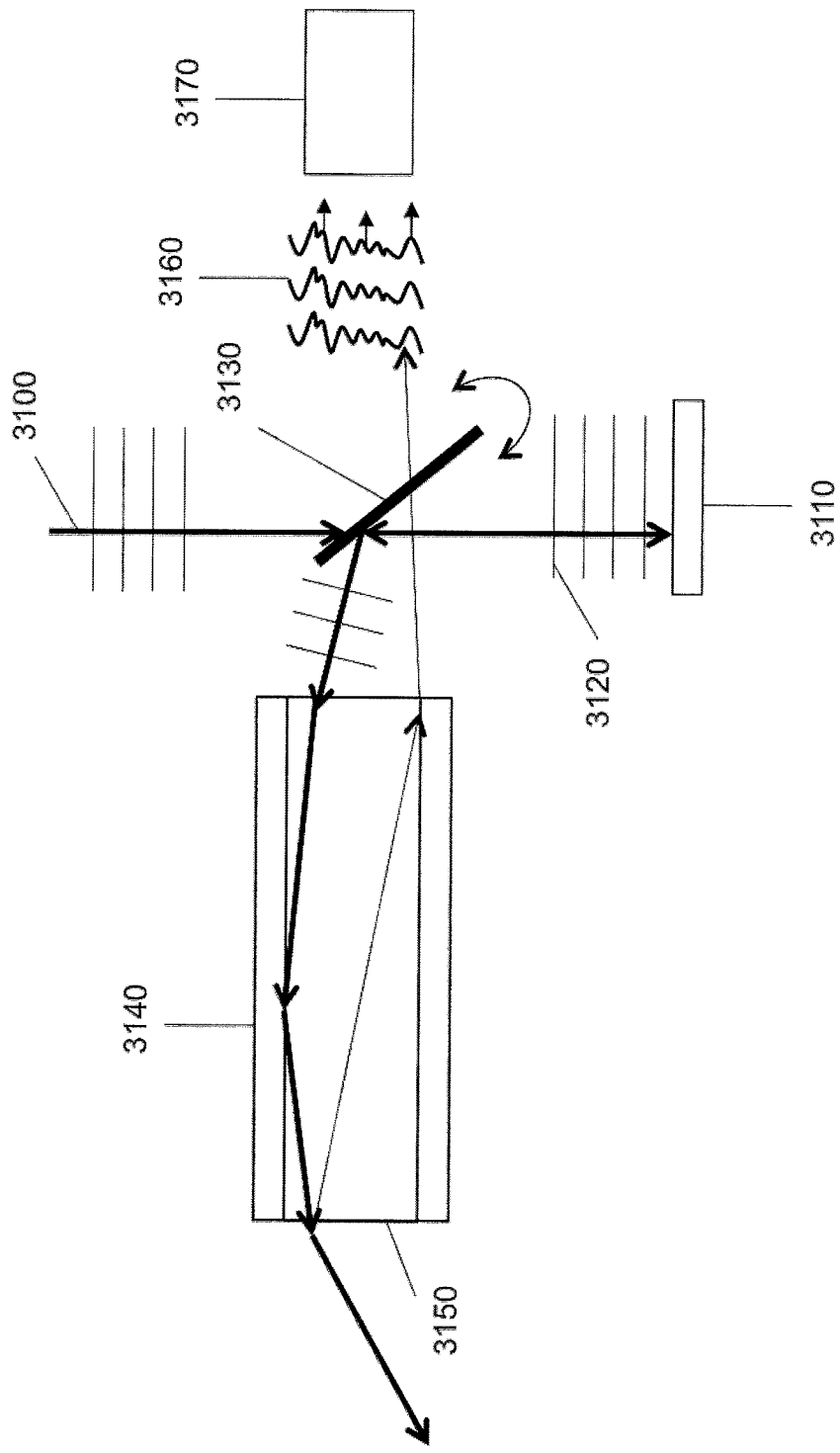
FIG. 31 shows a schematic to calibrate a flexible waveguide element by use of a partially reflective mirror on the distal tip of the multimode waveguide element.

FIG. 31 shows a schematic for calibrating a multimode waveguide element from one side. A plane wave 3100 is incident on a spatial light modulator 3110 which can also be any device that deflects a beam such as, but not limited to, a rotatable mirror, an acousto-optic deflector, an electro-optic deflector. A plane wave 3120 is diffracted or deflected by element 3110 towards a beam-splitter 3130 that redirects the plane wave in the core of a multimode waveguide element 3140. The distal end facet 3150 of the multimode waveguide 3140 has a partially reflective layer or simply reflective by Fresnel reflection. The reflected wavefront gets scrambled twice through the multimode waveguide 3140. The speckled output waveform 3160 is interfered with reference 3100. Phase and amplitude are recovered from the interferogram with device 3170. The process is repeated with multiple angles imparted on the beam 3100. The transmission matrix of twice the propagation is then recovered. Because the return path follows the same waveguide element, the transmission matrix for single path is recovered.

Figure 32:
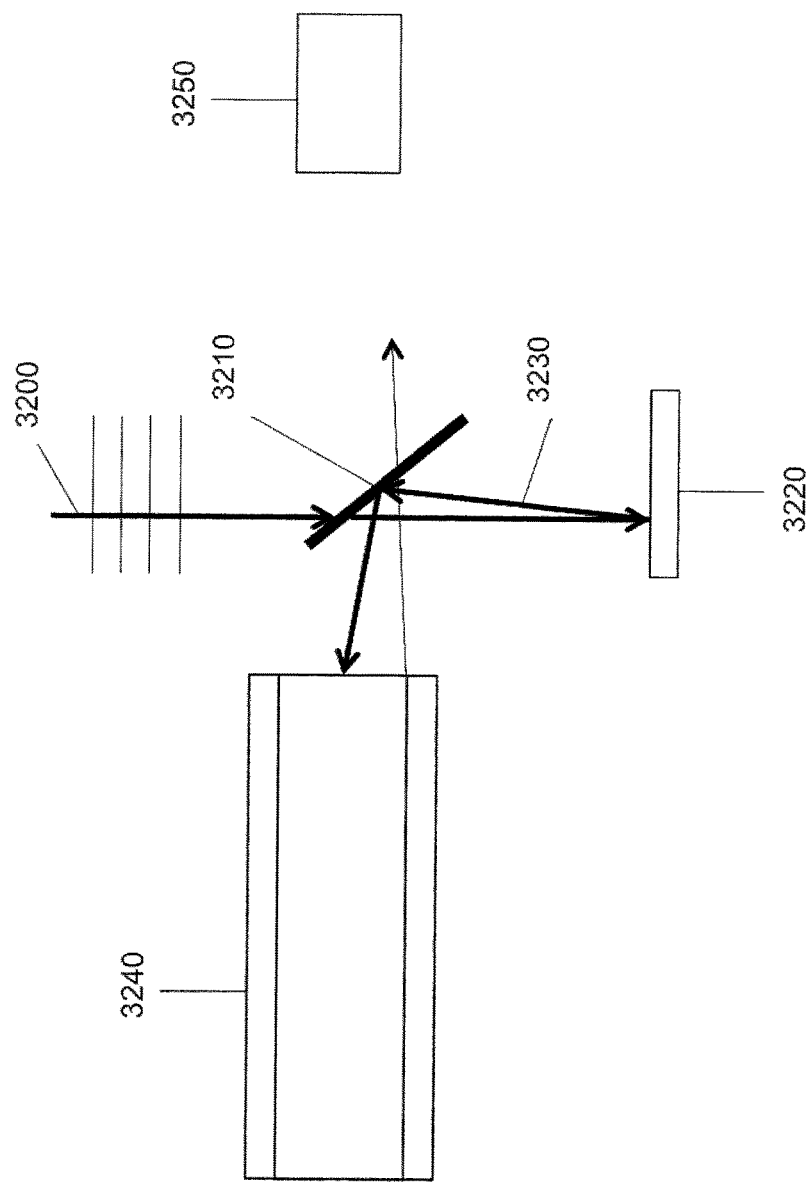
FIG. 32 shows a schematic for a beam-splitter that efficiently transmits the reference beam and efficiently reflects the counter-propagating diffracted beam from the SLM.

FIG. 32 shows a system to efficiently couple a phase conjugated light beam in a multimode waveguide element. A plane wave beam 3200 is incident on a beam-splitter 3120 at an angle such that the beam-splitter transmits efficiently (>90%) beam 3200. The phase-conjugated beam 3230 is diffracted at a small angle, typically a few degrees only and is directed back to beam-splitter 3210. The angular selectivity of beam-splitter 3210 is such that it reflects efficiently (>80%) beam 3230 and directs it to the multimode waveguide element 3240. Beam 3230 is deflected by element 3220 back to beam-splitter 3210. Thus the efficiency of the system is the product of the transmission of beam 3200, the diffraction efficiency of the spatial light modulator and the reflection of beam 3230 by the beam-splitter. In one instance, beam splitter 3210 is a thick reflection Bragg grating made from polymer or glass or crystal material. Thick reflection Bragg gratings are well known to be highly angularly selective. In another instance a reflective thin film filter, narrowband or edge is used with the appropriate angular selectivity. Phase and amplitude can be recovered from the interferogram with device 3250.

Figure 33:
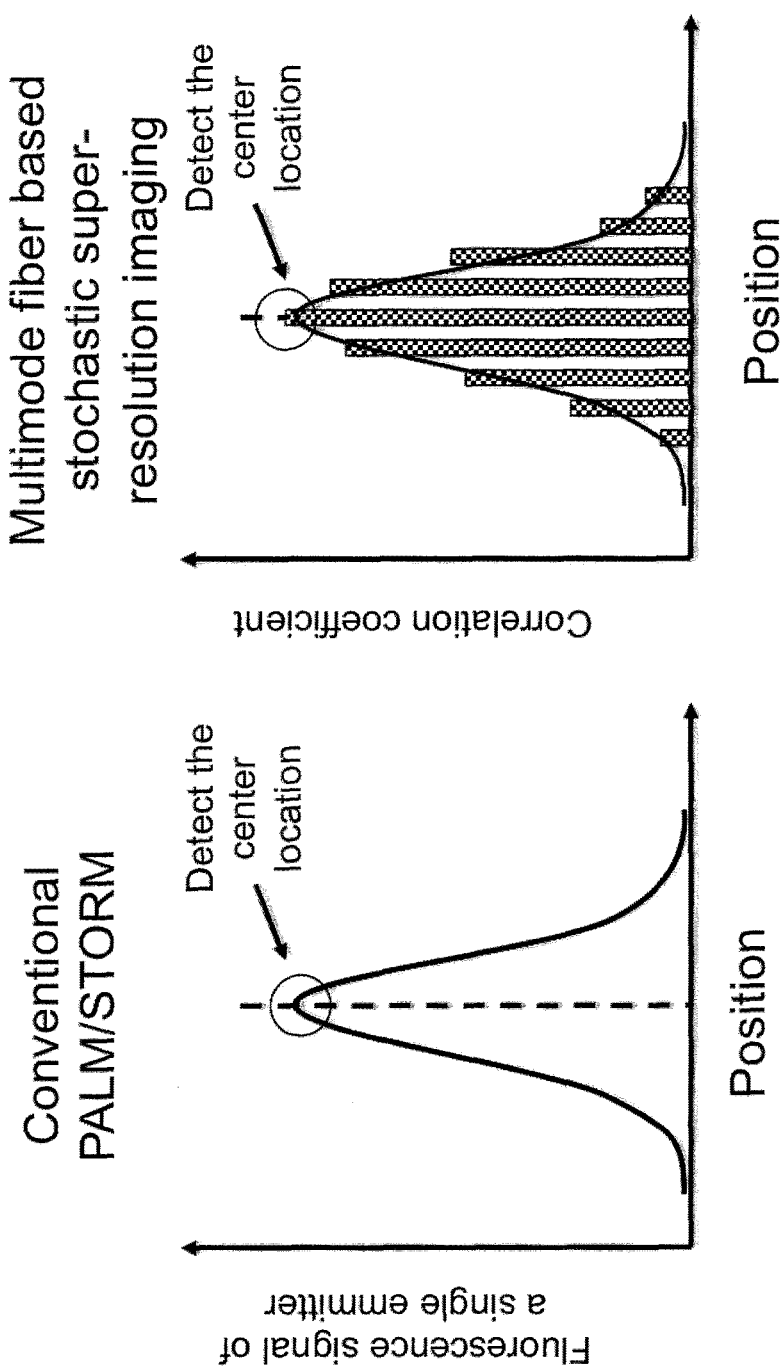
FIG. 33 shows the principle of super-resolution imaging based on a stochastic illumination.

FIG. 33 shows the principle of super-resolution imaging based on a stochastic illumination.

In conventional STORM/PALM imaging, fluorophores are sequentially activated. In each sequence, a few numbers of them emit a fluorescence signal from which the center location of the emitter is found. This process is repeated numerous times in order to build an image, which is the superposition of the locations of all the single emitters in the sample. For the multimode fiber based implementation of this method, a database of known speckle patters corresponding to different positions in the space are previously recorded. Then, for each activation sequence of emitters, the signal captured though the multimode fiber, which is but not limited to a fluroescence signal or a linear scattering signal, is compared to all the speckle patters in the database. From this comparison, a map of the correlation coefficent is extracted and interpolated. The maximum of this discrete interpolation corresponds to the location of the emitter. As for conventional stochastic illumination imaging technique, a high-resolution image can be constructed based on the locations of single emitters.

The forgoing description of the preffered emobodiment of the invention has been presented for the purposes of illustration and description. It is not intended to be exhaustive or to limit the invention to the precise for disclosed. Many modifications and variations are possible in light of the above teaching. It is intended that the scope of the invention be limited not by this detailed description, but rather by the claims appended hereto.

The invention claimed is:

1. A method for deterministic light transmission through a multimode waveguide comprising the steps of:
   providing the multimode waveguide;
   calibrating the multimode waveguide, the calibrating including,
      coupling in light at a proximal side of the multimode waveguide; and
      analyzing light at a distal side of the multimode waveguide by capturing one or more off-axis calibration interferogram images with a two-dimensional detector, and
   conditioning the distal side of the multimode waveguide by controlling a spatial light modulator at the proximal side with a conditioning pattern computed from the off-axis calibration interferogram images at the proximal side of the multimode waveguide to generate a counter-propagated beam.

2. The method of claim 1, wherein the distal side of the multimode waveguide is an opposite end of the multimode waveguide to the proximal side or a same side as the proximal side.

3. The method of claim 1, wherein the step of calibrating is realized through transmission matrix measurement.

4. The method of claim 1, further comprising
   adjusting a focal spot at the distal side of the multimode waveguide by digitally controlling the spatial light modulator in the conditioning step,
   directing the focal spot exiting the distal side of the multimode waveguide to a sample, and
   illuminating the sample by scanning the focal spot on the sample.

5. The method of claim 4, further comprising
   collecting light arriving from the sample as a result of illuminating, at the distal side of the multimode waveguide,
   sampling the collected light for determined scanning positions, whereby each determined scanning position represents a pixel, and
   constructing an image of the sample pixel by pixel, the pixels corresponding to the collected light at each determined scanning position.

6. The method of claim 5, further comprising achieving super-resolution by exciting the sample with a first wavelength and depleting with a second wavelength with a determined ring pattern.

7. The method of claim 4, further comprising steps of
   placing a scattering medium at the distal side of the multimode waveguide to decrease the size of the focal spot on the sample;
   choosing a size of the focal spot at the distal side of the multimode waveguide; and
   choosing a position of the focal spot at the distal side of the multimode waveguide.

8. The method of claim 1, further comprising steps of:
   directing light to a sample;
   analyzing scrambled light collected through the multimode waveguide from a sample to recover an image;
   analyzing light collected from the sample to extract axial information; and
   constructing an image of the sample in three dimensions, the axial dimension corresponding to different depths in the sample.

9. The method of claim 8, further comprising achieving super-resolution by projecting determined spatial patterns computed from the off-axis calibration interferogram images at the step of conditioning the waveguide.

10. The method of claim 8, further comprising achieving super-resolution by stochastically illuminating the sample when directing light from the distal side of the waveguide.

11. The method of claim 1, further comprising steps of
    providing light pulses at the step of coupling in light; and
    providing short light pulses at the distal side of the multimode waveguide by applying an appropriate light field at the step of conditioning the waveguide when controlling the spatial light modulator.

12. The method of claim 11, further comprising steps of
    determining a wavelength required for excitation of the sample; and
    choosing a wavelength twice the wavelength required for excitation of the sample for the light at the step of providing light pulses.

13. The method of claim 1, wherein the multimode waveguide is a rigid waveguide, the method further comprising
    positioning the distal side of the multimode waveguide on a surface of a sample.

14. The method of claim 1, wherein the multimode waveguide is a flexible waveguide, the method further comprising
    inserting the multimode waveguide in a sample and moving the multimode waveguide while adapting the conditioning pattern on the spatial light modulator in the step of conditioning the distal side.

15. The method of claim 1, further comprising
    calibrating the multimode waveguide from the proximal side to create calibrated light at the proximal side.

16. The method of claim 15, further comprising:
    providing a beacon means whereby the step of coupling comprises coupling light from the beacon means.

17. The method of claim 1, further comprising
    controlling the polarization of light at the distal side of the multimode waveguide;

analyzing light coupled in at the proximal side of the waveguide, at the distal side for all the polarizations; and conditioning the distal side of the multimode waveguide for all the polarizations.

18. The method of claim 1, further comprising transmitting high speed digital information.

19. The method of claim 1, wherein the multimode waveguide is an optical waveguide that presents modal scrambling and high dispersion, wherein the multimode waveguide is at least one item in the following list:
a step-index fiber,
a graded index fiber,
a double-clad fiber,
a large mode area fiber,
a fiber bundle,
a no-core fiber, and
a rod.

20. The method of claim 1, wherein the step of conditioning the output further includes:
processing the off-axis calibration interferogram image to retrieve phases of the counter-propagated output beam at the distal side of the multimode waveguide.

21. A system for deterministic light transmission through a multimode waveguide, the system comprising:
the multimode waveguide,
calibrating means configured for calibrating the multimode waveguide,
the calibrating means comprising,
light coupling means for coupling light at an input side of the multimode waveguide,
analyzing means arranged for analyzing light at an output side of the multimode waveguide,
the analyzing means comprising,
a digital analyzing system that digitally analyzes a complex light field in its phase or amplitude properties by capturing one or more off-axis calibration interferogram images with a two-dimensional detector, and
conditioning means configured to condition an output of the multimode waveguide,
the conditioning means comprising,
a spatial light modulator configured to project a light field computed from the off-axis calibration interferogram images at the input side of the multimode waveguide.

22. The system of claim 21, wherein the multimode waveguide is an optical waveguide that presents modal scrambling and high dispersion, wherein the multimode waveguide is at least one item in the following list:
a step-index fiber,
a graded index fiber,
a double-clad fiber,
a large mode area fiber,
a fiber bundle,
a no-core fiber, and
a rod.

23. The system of claim 21, wherein the spatial light modulator is at least one item of the following list:
a phase liquid crystal spatial light modulator,
a deformable mirror,
a binary amplitude modulator, and
an analog amplitude modulator.

24. The system of claim 21, wherein the output side of the multimode waveguide is either
an opposite end of the waveguide to the input side, or
the same side as the input side.

25. The system of claim 21, wherein the digital analyzing system comprises a coherent holographic system.

26. The system of claim 21, wherein the digital analyzing system comprises an incoherent system.

27. The system of claim 21, wherein the conditioning means are further configured to adjust a focal spot at the output side of the multimode waveguide by digital control of the spatial light modulator, the system further comprising
directing means configured to direct the focal spot exiting the output side of the multimode waveguide to a sample, and
scanning means configured to illuminate the sample by scanning the focal spot on the sample.

28. The system of claim 27, further comprising
collecting means configured to collect light arriving from the sample as a result of illuminating, at the output side of the multimode waveguide,
sampling means configured to sample the collected light for determined scanning positions, whereby each determined scanning position represents a pixel, and
image constructing means configured to construct an image of the sample pixel by pixel, the pixels corresponding to the collected light at each determined scanning position.

29. The system of claim 28, further comprising
an appropriate filter configured to separate light collected from the sample from excitation light by directing the light arriving from the sample.

30. The system of claim 28, further comprising
a spectrometer, and
directing means configured to direct Raman light arriving from the sample to the spectrometer.

31. The system of claim 21, further comprising
beacon means configured to calibrate the multimode waveguide from a same side as the input side in real-time,
the beacon means comprising
a beacon light source arranged such that light from the beacon light source is coupled by the light coupling means.

32. The system of claim 31, wherein the beacon light source is one of
a focus spot generated by an objective lens,
a specified light pattern,
multiple foci spots, and
a virtual beacon light source generated by a device at the distal end of the multimode fiber.

33. The system of claim 32, further comprising
means for generating the virtual beacon light source, comprising
excitation means for providing excitation light from the same side as the input side of the multimode waveguide, and
second analyzing means at the input side of the multimode waveguide for recording the light pattern generated by the beacon light source after propagating through the multimode waveguide.

34. The system of claim 33 wherein the excitation means are provided by one of
a co-propagating single mode fiber,
a plurality of co-propagating single mode fibers, and
a co-propagating single mode core in a double-clad multimode waveguide.

35. The system of claim 33 further comprising means configured to compare the analyzed light pattern with a database of light patterns corresponding to different configurations of the multimode waveguide.

36. The system of claim 32, wherein the device is one of the items of the following list:
  micro-lens; and
  a hologram.

37. The system of claim 21, wherein the conditioning means is configured to process the off-axis calibration interferogram image to retrieve phases of the counter-propagated output beam at the output of the multimode waveguide.

38. A method for deterministic light transmission through a multimode waveguide comprising the steps of:
  calibrating the multimode waveguide, the calibrating including,
    coupling in light at an input side of the multimode waveguide, and
    analyzing light coupled in at the input side of the multimode waveguide, at an output side of the multimode waveguide;
  conditioning the output of the multimode waveguide by controlling a spatial light modulator to choose an appropriate light field at the proximal tip of the multimode waveguide;
  adjusting a focal spot at the output side of the multimode waveguide by digitally controlling the spatial light modulator in the conditioning step;
  directing the focal spot exiting the output side of the multimode waveguide to a sample;
  illuminating the sample by scanning the focal spot on the sample;
  placing a scattering medium at the output side of the multimode waveguide to decrease the size of the focal spot on the sample;
  choosing a size of the focal spot at the output side of the multimode waveguide; and
  choosing a position of the focal spot at the output side of the multimode waveguide.

39. A method for deterministic light transmission through a multimode waveguide comprising the steps of:
  calibrating the multimode waveguide, the calibrating including,
    coupling in light at an input side of the multimode waveguide, the input light having a known amplitude and phase,
    analyzing light at an output side of the multimode waveguide by capturing off-axis calibration interferogram images with a two-dimensional detector, and
    computing the transmission matrix of the multimode waveguide from the light of the set of coupling and the off-axis calibration interferogram images; and
  conditioning the output side of the multimode waveguide by controlling a spatial light modulator with an appropriate light amplitude and phase computing with the transmission matrix at the input side of the multimode waveguide.

* * * * *